United States Patent
Balan et al.

(10) Patent No.: US 9,669,038 B1
(45) Date of Patent: *Jun. 6, 2017

(54) HETEROCYCLIC COMPOUNDS AND USES THEREOF

(71) Applicant: Globavir BioSciences, Inc., Los Altos, CA (US)

(72) Inventors: Chenera Balan, Thousand Oaks, CA (US); Usha Nagavarapu, San Jose, CA (US)

(73) Assignee: GLOBAVIR BIOSCIENCES, INC., Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/923,292

(22) Filed: Oct. 26, 2015

Related U.S. Application Data

(63) Continuation of application No. 13/951,335, filed on Jul. 25, 2013, now Pat. No. 9,321,749.

(60) Provisional application No. 61/675,783, filed on Jul. 25, 2012.

(51) Int. Cl.
| | | |
|---|---|---|
| *C07D 403/06* | (2006.01) | |
| *C07D 401/06* | (2006.01) | |
| *A61K 31/541* | (2006.01) | |
| *A61K 31/5377* | (2006.01) | |
| *A61K 31/496* | (2006.01) | |

(52) U.S. Cl.
CPC .......... *A61K 31/541* (2013.01); *A61K 31/496* (2013.01); *A61K 31/5377* (2013.01)

(58) Field of Classification Search
CPC ... C07D 403/06; C07D 401/06; A61K 31/541
USPC ............ 514/252.11, 252.12, 252.13, 255.02
See application file for complete search history.

(56) References Cited

U.S. PATENT DOCUMENTS

| | | | |
|---|---|---|---|
| 4,158,707 A | 6/1979 | Steffen et al. | |
| 4,309,421 A | 1/1982 | Ghyczy et al. | |
| 4,992,445 A | 2/1991 | Lawter et al. | |
| 5,001,139 A | 3/1991 | Lawter et al. | |
| 5,023,252 A | 6/1991 | Hseih | |
| 5,059,421 A | 10/1991 | Loughrey et al. | |
| 5,164,405 A | 11/1992 | McFarlane et al. | |
| 5,244,925 A | 9/1993 | Wretlind et al. | |
| 5,631,237 A | 5/1997 | Dzau et al. | |
| 5,643,599 A | 7/1997 | Lee et al. | |
| 5,653,996 A | 8/1997 | Hsu | |
| 5,681,811 A | 10/1997 | Ekwuribe | |
| 5,817,789 A | 10/1998 | Heartlein et al. | |
| 5,885,613 A | 3/1999 | Holland et al. | |
| 9,321,749 B1 * | 4/2016 | Balan | C07D 403/06 |
| 2006/0287221 A1 | 12/2006 | Knudsen et al. | |
| 2010/0281003 A1 | 11/2010 | Jochim et al. | |

FOREIGN PATENT DOCUMENTS

WO WO-2004037797 A2 5/2004

OTHER PUBLICATIONS

Bangham, et al. Diffusion of univalent ions across the lamellae of swollen phospholipids. JMolBiol. 13(1):238-52 (1965).
Evans, et al. Enantioselective aldol condensations. 2. Erythro-selective chiral aldol condensations via boron enolates. J. Am. Chem. Soc. 103(8):2127-2129 (1981).
Forsythe, et al. Activation of vascular endothelial growth factor gene transcription byhypoxia-induciblefactor1. MolCellBiol. 16(9):4604-13 (1996).
Ivan, et al. HIFalpha targeted for VHL-mediated destruction by proline hydroxylation: implications for O2 sensing. Science. 292(5516):464-8 (2001).
Joliot, et al. Transduction peptides: from technology to physiology. NatCellBiol. 6(3):189-96 (2004).
Lando, et al. FIH-1 is an asparaginyl hydroxylase enzyme that regulates the transcriptional activity of hypoxia-inducible factor. Genes Dev. 16(12):1466-71 (2002).
Lao, et al. In vivo modulation of hypoxia-inducible signaling by topographical helix mimetics. Proc Natl Acad Sci USA. 111(21):7531-6 (2014). doi:10.1073/pnas.1402393111.
Okino, et al. Hypoxia-inducible mammalian gene expression analyzed in vivo at a TATA-driven promoter and at an initiator-driven promoter. JBiolChem. 3(37):238 37-43 (1998).
Roberts. Buyer's Guide to Protein Transduction Reagents. Scientist, 18:42-3 (2004).
U.S. Appl. No. 13/951,335 Non Final Office Action mailed Feb. 9, 2015.
U.S. Appl. No. 13/951,335 Ex Parte Quayle Action mailed Jul. 28, 2015.
Wang, et al. pH-sensitive immunoliposomes mediate target-cell-specific delivery and controlled expression of a foreign gene in mouse. Proc Natl Acad Sci USA. 84(22):7851-5 (1987).
Wender, et al. The design, synthesis, and evaluation of molecules that enable or enhance cellular uptake: peptoid molecular transporters. Proc Natl Acad Sci USA. 97(24):13003-8 (2000).
Wolff, et al. The use of monoclonalanti-Thy1 IgG1 for the targeting of liposomes to AKR-A cells in vitro and in vivo. Biochim Biophys Acta. 802(2):259-73 (1984).
Wood, et al., The role of the aryl hydrocarbon receptor nuclear translocator (ARNT) in hypoxic induction of gene expression. Studies in ARNT-deficient cells. J Biol Chem. 271(25):15117-23 (1996).

* cited by examiner

*Primary Examiner* — Kahsay Habte
(74) *Attorney, Agent, or Firm* — Wilson Sonsini Goodrich & Rosati

(57) ABSTRACT

Disclosed herein are novel heterocyclic compounds, their salts, pharmaceutical compositions comprising such compounds and salts, and their uses in modulating protein-protein interactions and for treating diseases resulting from aberrant protein-protein interactions.

12 Claims, 14 Drawing Sheets

HETEROCYCLIC COMPOUNDS AND USES THEREOF

CROSS REFERENCE

This application is a continuation of U.S. patent application Ser. No. 13/951,335 filed Jul. 25, 2013 which claims the benefit of U.S. Provisional Application No. 61/675,783, filed Jul. 25, 2012 which is incorporated herein by reference in its entirety.

BACKGROUND

Protein-protein interaction plays an important role in a variety of biological processes, such as angiogenesis, glucose homeostasis, mitochondrial biogenesis, adipogenesis, cell proliferation, differentiation, apoptosis, and tumorigenesis. Many human diseases are the result of abnormal protein-protein interactions involving endogenous proteins, proteins from pathogens or both. Therefore, the inhibition of these aberrant associations is clinically significant.

Currently, at least 400 individual proteins are considered to be viable drug targets, and it is estimated that the number of disease-related genes could be greater than about 10,000. Sequence analysis of these proteins shows that the majority of targets fall within a few major gene families (e.g., GPCRs, kinases, proteases and peptidases). However, protein-protein interaction presents a significant hurdle for current drug discovery efforts. In particular, targeting protein-protein interaction involving large contact areas with required specificity is challenging.

Among such protein-protein interactions, α-helices play fundamental roles in mediating protein-protein interactions. Examination of complexes of proteins with other biomolecules reveals that often one or more faces of the helix are involved in binding. As such, synthetic scaffolds that display protein-like functionality and reproduce the arrangement of key side chains on an a-helix would be invaluable as therapeutics for treating diseases associated with aberrant protein-protein interaction.

The present invention addresses this need among others.

SUMMARY OF THE INVENTION

In one aspect, the present invention provides a compound of formula I:

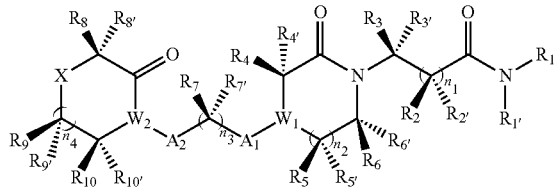

or a pharmaceutically acceptable salt thereof, wherein each of $R_1$ and $R_{1'}$ is independently selected from the group consisting of H, alkyl, cycloalkyl and heteroalkyl or $R_1$, $R_{1'}$ and the N they are attached to in combination form the structure

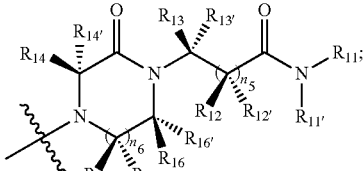

each of $R_{11}$ and $R_{11'}$ is independently selected from the group consisting of H, alkyl, cycloalkyl and heteroalkyl;

each of $n_1$, $n_3$ and $n_5$ is independently 0 or 1;

each of $n_2$, $n_4$ and $n_6$ is independently 0, 1, 2 or 3;

$A_1$-$W_1$ is selected from

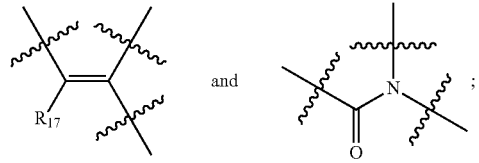

$W_2$-$A_2$ is selected from

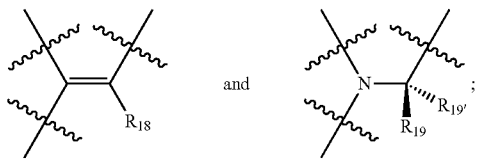

each of $R_2$, $R_{2'}$, $R_3$, $R_{3'}$, $R_4$, $R_{4'}$, $R_5$, $R_{5'}$, $R_6$, $R_{6'}$, $R_7$, $R_{7'}$, $R_8$, $R_{8'}$, $R_9$, $R_{9'}$, $R_{10}$, $R_{10'}$, $R_{12}$, $R_{12'}$, $R_{13}$, $R_{13'}$, $R_{14}$, $R_{14'}$, $R_{15}$, $R_{15'}$, $R_{16}$, $R_{16'}$, $R_{17}$, $R_{18}$, $R_{19}$ and $R_{19'}$ is independently selected from the group consisting of H, alkyl, cycloalkyl, heteroalkyl, alkylamine, alkylhydroxyl, alkylthiol, alkylcarboxylic acid, alkylamide, alkylguanidine, aryl, heteroaryl, alkylaryl, alkylheteroaryl and an amino acid side chain;

X is selected from the group consisting of O, S, S(O), S(O)$_2$, —NR$_{21}$, —NC(=O)R$_{22}$, —NS(=O)$_2$NR$_{23}$R$_{24}$, —NS(=O)$_2$R$_{25}$ and —NC(=O)NR$_{26}$R$_{27}$;

each of $R_{21}$, $R_{22}$, $R_{23}$, $R_{24}$, $R_{25}$, $R_{26}$ and $R_{27}$ is independently selected from the group consisting of H, alkyl, cycloalkyl, heteroalkyl, aryl, heteroaryl, and any pair of $R_{23}$/$R_{24}$ and $R_{26}$/$R_{27}$ may optionally form a 5-8 membered, substituted or unsubstituted, saturated or unsaturated, heterocyclic or carbocyclic ring; and when (i) each of $n_2$, $n_4$ and $n_6$ is 1; (ii) each of $n_1$ and $n_3$ is 0; (iii) $A_1$-$W_1$ is

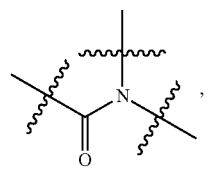 [SMILES: *C(=O)N(*)*]

and (iv) $W_2$-$A_2$ is

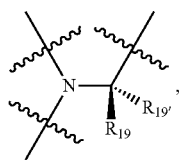

then X is selected from the group consisting of O, S, S(O), $S(O)_2$, $-NS(=O)_2NR_{23}R_{24}$ and $-NS(=O)_2R_{25}$.

In another aspect, the present invention provides a compound of formula II:

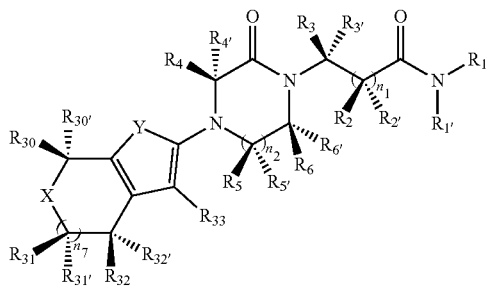

or a pharmaceutically acceptable salt thereof, wherein
Y is selected from the group consisting of O, S, $-NR_{34}$;
each of $R_1$ and $R_{1'}$ is independently selected from the group consisting of H, alkyl, cycloalkyl and heteroalkyl or $R_1$, $R_{1'}$ and the N they are attached to in combination form the structure

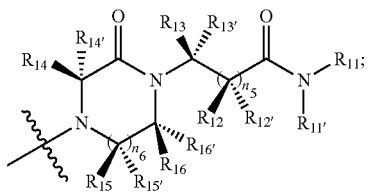

each of $R_{11}$ and $R_{11'}$ is independently selected from the group consisting of H, alkyl, cycloalkyl and heteroalkyl;
each of $n_1$ and $n_5$ is independently 0 or 1;
each of $n_2$ and $n_6$ is independently 1, 2 or 3;
$n_7$ is 0, 1, 2 or 3;
each of $R_2$, $R_{2'}$, $R_3$, $R_{3'}$, $R_4$, $R_{4'}$, $R_5$, $R_{5'}$, $R_6$, $R_{6'}$, $R_{12}$, $R_{12'}$, $R_{13}$, $R_{13'}$, $R_{14}$, $R_{14'}$, $R_{15}$, $R_{15'}$, $R_{16}$, $R_{16'}$, $R_{30}$, $R_{30'}$, $R_{31}$, $R_{31'}$, $R_{32}$, $R_{32'}$ and $R_{34}$ is independently selected from the group consisting of H, alkyl, cycloalkyl, heteroalkyl, alkylamine, alkylhydroxyl, alkylthiol, alkylcarboxylic acid, alkyl amide, alkylguanidine, aryl, heteroaryl, alkylaryl, alkylheteroaryl and an amino acid side chain; $R_{33}$ is selected from the group consisting of H, $-NO_2$, $-OCF_3$, $-CN$, alkyl, cycloalkyl, amino, hydroxyl, halogen, aryl, heteroaryl, alkylamine, alkylhydroxy, alkylthiol, alkylcarboxylic acid, alkylamide, alkylguanidine, aryl, heteroaryl, alkylaryl and alkylheteroaryl;
X is selected from the group consisting of O, S, S(O), $S(O)_2$, $-NR_{21}$, $-NC(=O)R_{22}$, $-NS(=O)_2NR_{23}R_{24}$, $-NS(=O)_2R_{25}$, and $-NC(=O)NR_{26}R_{27}$; and
each of $R_{21}$, $R_{22}$, $R_{23}$, $R_{24}$, $R_{25}$, $R_{26}$ and $R_{27}$ is independently selected from the group consisting of H, alkyl, cycloalkyl, heteroalkyl, aryl, heteroaryl, and any pair of $R_{23}/R_{24}$ and $R_{26}/R_{27}$ may optionally form a 5-8 membered, substituted or unsubstituted, saturated or unsaturated, heterocyclic or carbocyclic ring.

In another aspect, there is provides a compound of formula III:

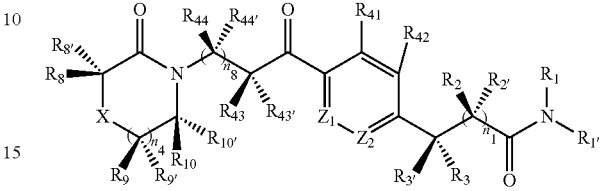

or a pharmaceutically acceptable salt thereof, wherein
each of $R_1$ and $R_{1'}$ is independently selected from the group consisting of H, alkyl, cycloalkyl and heteroalkyl or $R_1$, $R_{1'}$ and the N they are attached to in combination form the structure

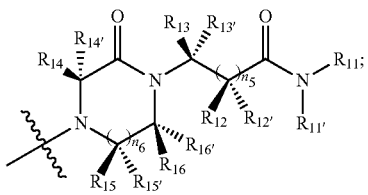

each of $R_{11}$ and $R_{11'}$ is independently selected from the group consisting of H, alkyl, cycloalkyl and heteroalkyl;
each of $Z_1$ and $Z_2$ is independently N or $-CR_{45}$;
each of $R_{41}$, $R_{42}$ and $R_{45}$ is independently selected from the group consisting of H, $-NO_2$, $-OCF_3$, $-CN$, alkyl, cycloalkyl, amino, hydroxyl, halogen, aryl, heteroaryl, alkylamine, alkylhydroxyl, alkylthiol, alkylcarboxylic acid, alkylamide, alkylguanidine, aryl, heteroaryl, alkylaryl and alkylheteroaryl;
each of $R_2$, $R_{2'}$, $R_3$, $R_{3'}$, $R_8$, $R_{8'}$, $R_9$, $R_{9'}$, $R_{10}$, $R_{10'}$, $R_{12}$, $R_{12'}$, $R_{13}$, $R_{13'}$, $R_{14}$, $R_{14'}$, $R_{15}$, $R_{15'}$, $R_{16}$, $R_{16'}$, $R_{43}$, $R_{43'}$, $R_{44}$ and $R_{44'}$ is independently selected from the group consisting of H, alkyl, cycloalkyl, heteroalkyl, alkylamine, alkylhydroxy, alkylthiol, alkylcarboxylic acid, alkyl amide, alkylguanidine, aryl, heteroaryl, alkylaryl, alkylheteroaryl and an amino acid side chain;
each of $n_1$, $n_5$ and $n_8$ is independently 0 or 1;
each of $n_4$ and $n_6$ is independently 1, 2 or 3;
X is selected from the group consisting of O, S, S(O), $S(O)_2$, $-NR_{21}$, $-NC(=O)R_{22}$, $-NS(=O)_2NR_{23}R_{24}$, $-NS(=O)_2R_{25}$, and $-NC(=O)NR_{26}R_{27}$; and
each of $R_{21}$, $R_{22}$, $R_{23}$, $R_{24}$, $R_{25}$, $R_{26}$ and $R_{27}$ is independently selected from the group consisting of H, alkyl, cycloalkyl, heteroalkyl, aryl, heteroaryl, and any pair of $R_{23}/R_{24}$ and $R_{26}/R_{27}$ may optionally form a 5-8 membered, substituted or unsubstituted, saturated or unsaturated, heterocyclic or carbocyclic ring.

In yet another aspect, the present invention provides a compound of formula IV:

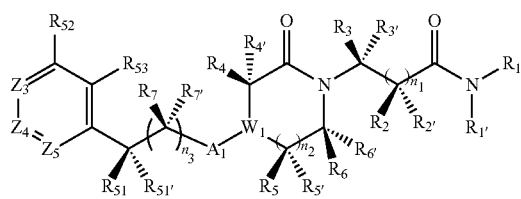

or a pharmaceutically acceptable salt thereof, wherein each of $R_1$ and $R_{1'}$ is independently selected from the group consisting of H, alkyl, cycloalkyl and heteroalkyl or $R_1$, $R_{1'}$ and the N they are attached to in combination form the structure

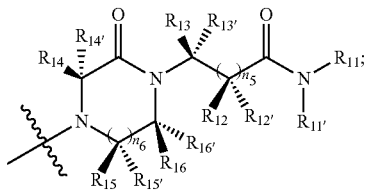

each of $R_{11}$ and $R_{11'}$ is independently selected from the group consisting of H, alkyl, cycloalkyl and heteroalkyl;
$Z_3$ is N or $-CR_{54}$;
$Z_4$ is N or $-CR_{55}$;
$Z_5$ is N or $-CR_{56}$;
each of $R_{52}$, $R_{53}$, $R_{54}$, $R_{55}$ and $R_{56}$ is independently selected from the group consisting of H, $-NO_2$, $-CN$, $-OCF_3$, alkyl, cycloalkyl, amino, hydroxyl, halogen, aryl, heteroaryl, alkylamine, alkylhydroxy, alkylthiol, alkylcarboxylic acid, alkyl amide, alkylguanidine, aryl, heteroaryl, alkylaryl, and alkylheteroaryl;
each of $n_1$, $n_3$ and $n_5$ is independently 0 or 1;
each of $n_2$ and $n_6$ is independently 1, 2 or 3;
$A_1$-$W_1$ is selected from

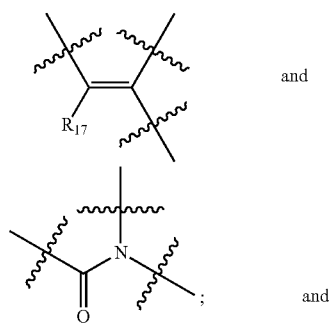

each of $R_2$, $R_{2'}$, $R_3$, $R_{3'}$, $R_4$, $R_{4'}$, $R_5$, $R_{5'}$, $R_6$, $R_{6'}$, $R_7$, $R_{7'}$, $R_{12}$, $R_{12'}$, $R_{13}$, $R_{13'}$, $R_{14}$, $R_{14'}$, $R_{15}$, $R_{15'}$, $R_{16}$, $R_{16'}$, $R_{17}$, $R_{51}$ and $R_{51'}$ is independently selected from the group consisting of H, alkyl, cycloalkyl, heteroalkyl, alkylamine, alkylhydroxy, alkylthiol, alkylcarboxylic acid, alkyl amide, alkylguanidine, aryl, heteroaryl, alkylaryl, alkylheteroaryl and an amino acid side chain.

In one aspect, the present invention provides a pharmaceutical composition comprising a compound or a pharmaceutically acceptable salt according to any one of formulas I-IV and a pharmaceutically acceptable carrier. The pharmaceutical composition may comprise additional excipient and/or binders.

In another aspect, the present invention provides a method of inhibiting a protein-protein interaction, comprising contacting at least one of the proteins involved in said protein-protein interaction with an effective amount of a compound or a pharmaceutically acceptable salt of formulas I-IV. In one embodiment, the proteins comprise HIF-1α and/or Hif-2α. In another embodiment, the protein-protein interaction is HIF-1α-p300 interaction. In yet another embodiment, the protein-protein interaction is HIF-1α-CREB-binding protein interaction.

In yet another aspect, the present invention provides a method of treating a disorder in a subject, comprising administering to the subject a therapeutically effective amount of a compound or a pharmaceutically acceptable salt of formulas I-IV or a pharmaceutical composition comprising the compound or pharmaceutically acceptable salt. In one embodiment, the disorder is cancer. In another embodiment, the disorder is autoimmune disease. In another embodiment, the disorder is infectious disease. In yet another embodiment, the disorder is metabolic disease. The treatment may involves treating an aberrant protein-protein interaction. In one embodiment, the aberrant protein-protein interaction involves HIF-1α and/or Hif-2α.

INCORPORATION BY REFERENCE

All publications, patents, and patent applications mentioned in this specification are herein incorporated by reference to the same extent as if each individual publication, patent, or patent application is specifically and individually indicated to be incorporated by reference.

Error bars represent ±s.e.m. of experiments performed in triplicates. * P<0.05, ** P<0.01, t-test, relative to sample Vehicle Hypoxia.

Figure 5:
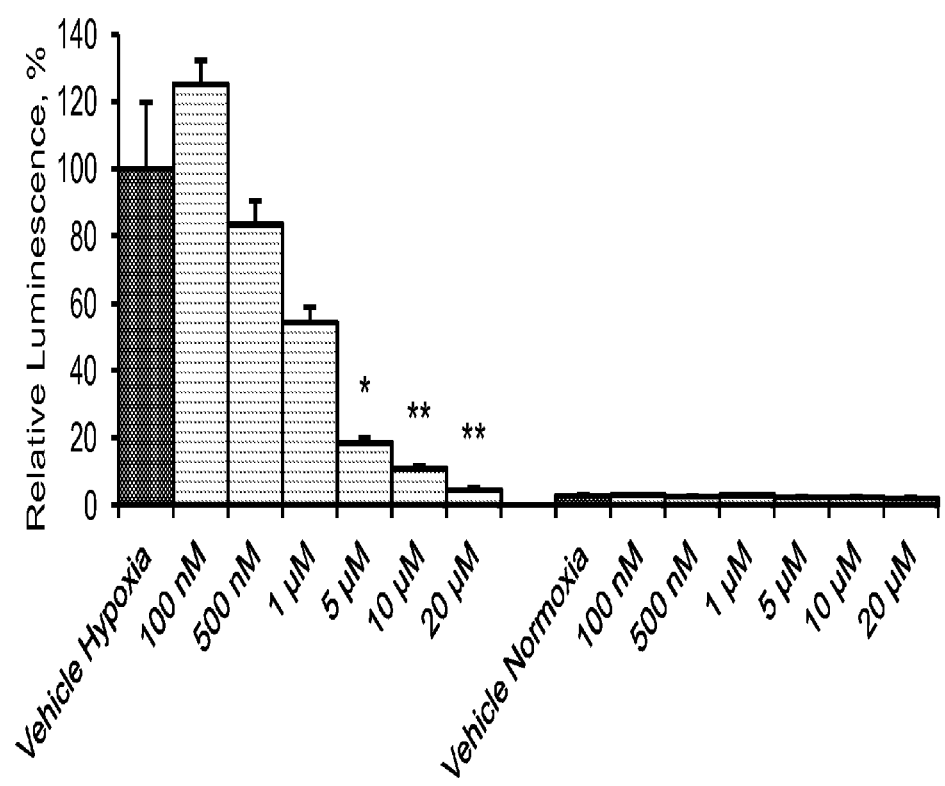

FIG. 5 shows that OOP 2 reduces HIF1α-inducible promoter activity in vitro in a dose-dependent manner. Results from the luciferase-based promoter activity assay with MDA-MB-231-HRE-Luc cell line treated with OOP 2 at various concentration. Hypoxia was mimicked by $O_2$ deprivation in a GasPak™ EZ Anaerobe Pouch System (BD). Error bars represent ±s.e.m. of experiments performed in triplicates. * P<0.05, ** P<0.01, t-test, relative to sample Vehicle Hypoxia.

Figure 6:
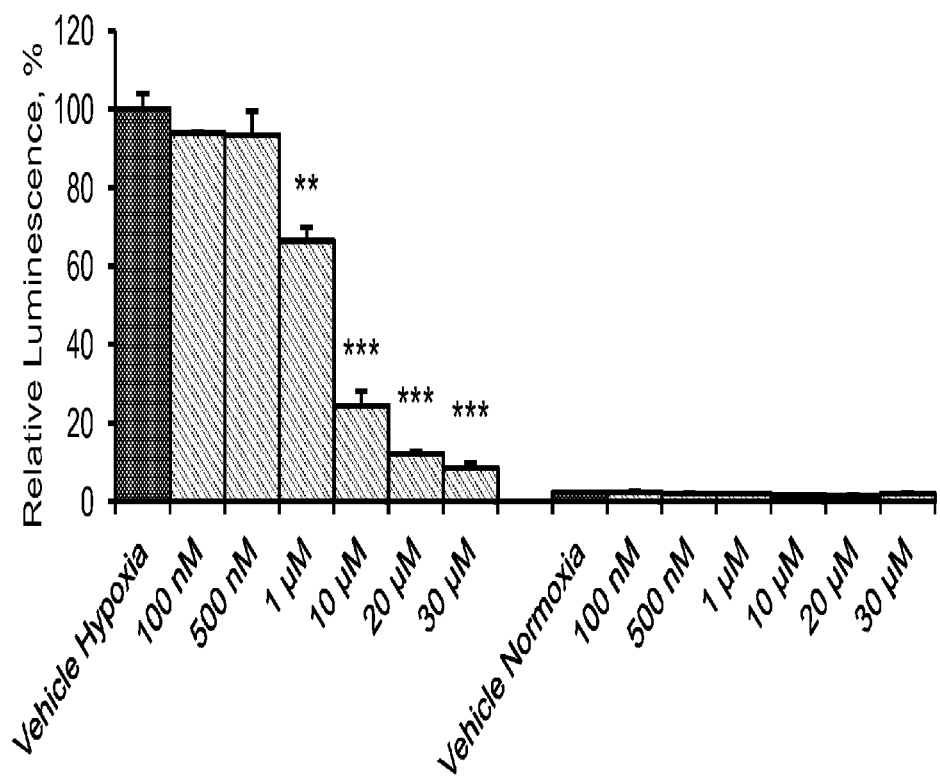

FIG. 6 shows that OOP 3 reduces HIF1α-inducible promoter activity in vitro in a dose-dependent manner. Results from the luciferase-based promoter activity assay with MDA-MB-231-HRE-Luc cell line treated with OOP 3 at various concentration. Hypoxia was mimicked by $O_2$ deprivation in a GasPak™ EZ Anaerobe Pouch System (BD). Error bars represent ±s.e.m. of experiments performed in triplicates.  P<0.01, * P<0.001, t-test, relative to sample Vehicle Hypoxia.

Figure 7:
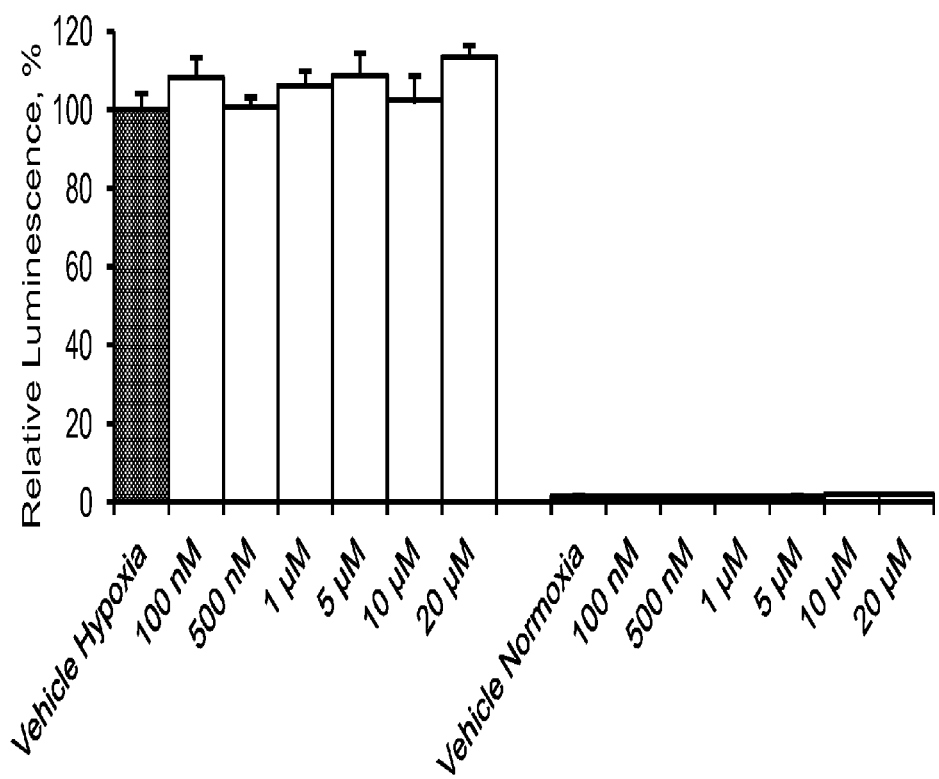

FIG. 7 shows that OOP 4 does not affect HIF1α-inducible promoter activity in vitro. Results from the luciferase-based promoter activity assay with MDA-MB-231-HRE-Luc cell line treated with OOP 4 at various concentration. Hypoxia was mimicked by $O_2$ deprivation in a GasPak™ EZ Anaerobe Pouch System (BD). Error bars represent ±s.e.m. of experiments performed in triplicates.

Figure 8:
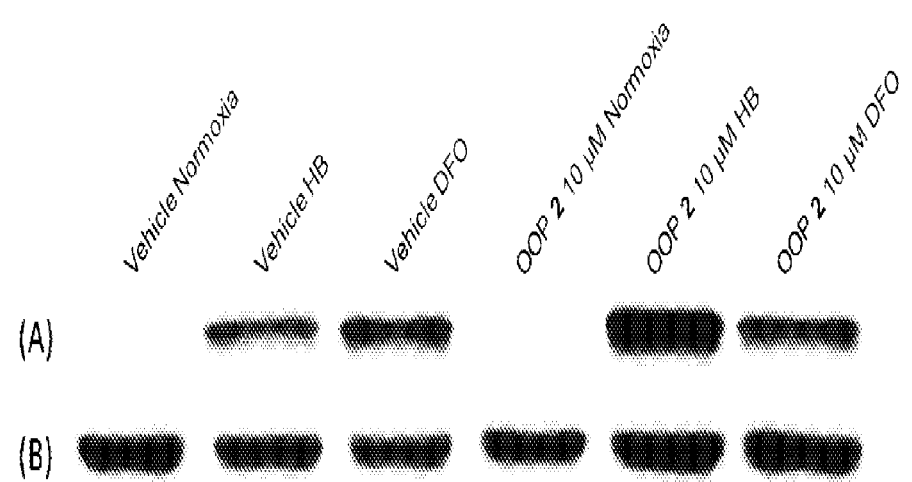

FIG. 8 shows that OOP 2 does not decrease the intracellular levels of HIF-1α. Western blot analysis of HIF-1α levels (A) with β-actin used as a control (B) in the whole cell extract of A549 cells. Cells were incubated for a total of 24 hours with OOP 2. After 6 h, hypoxia was mimicked by $O_2$ deprivation in a GasPak™ EZ Anaerobe Pouch System (BD) for an additional 18 h.

Figure 9:
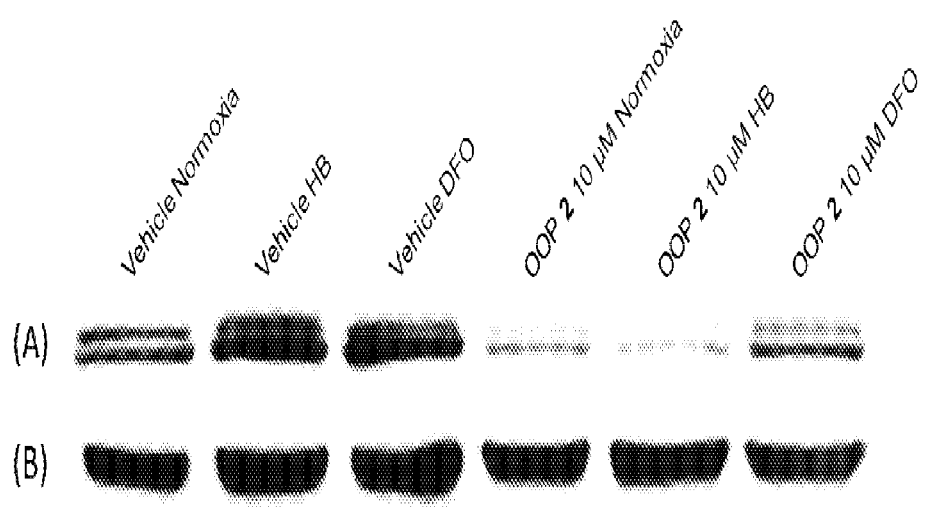

FIG. 9 shows that OOP 2 decreases intracellular levels of c-Met. Western blot analysis of c-Met levels (A) with β-actin used as a control (B) in the whole cell extract of A549 cells. Cells were incubated for a total of 24 hours with OOP 2. After 6 h, hypoxia was mimicked by $O_2$ deprivation in a GasPak™ EZ Anaerobe Pouch System (BD) for an additional 18 h.

Figure 10:
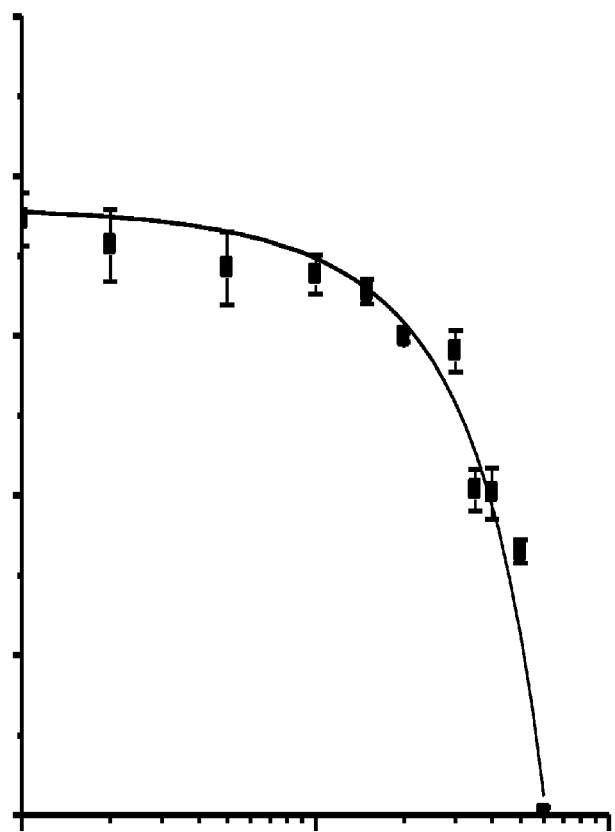

FIG. 10 shows low cytotoxicity of OOP 1. Results from the MTT assays in MCF7 cells treated with OOP 1 the range of concentrations of 1 μM and 60 μM for 48 h ($EC_{50}$=30 μM).

Figure 11:
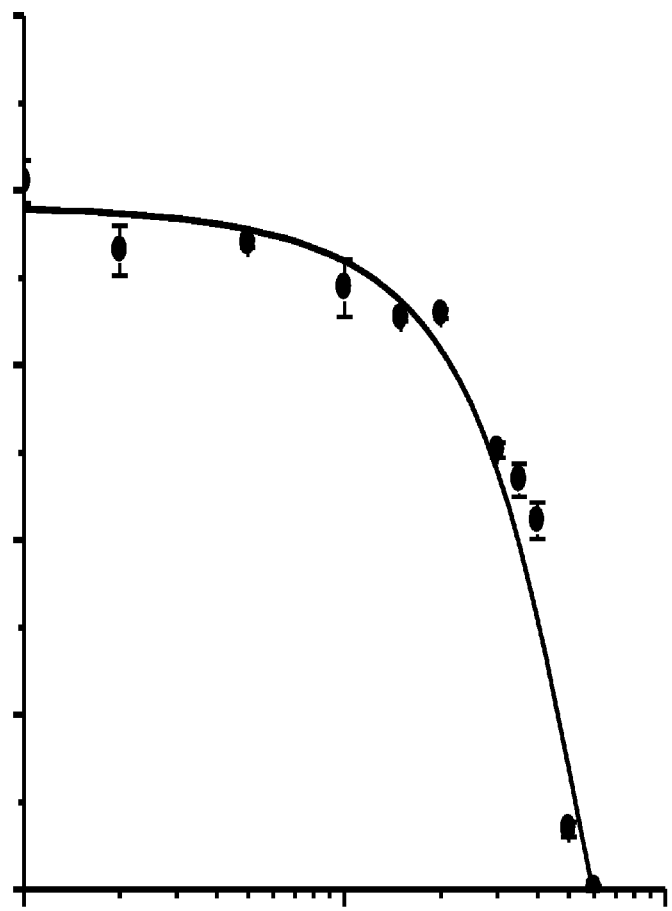

FIG. 11 shows low cytotoxicity of OOP 2. Results from the MTT assays in MCF7 cells treated with OOP 2 the range of concentrations of 1 μM and 60 μM for 48 h ($EC_{50}$=30 μM).

Figure 12:
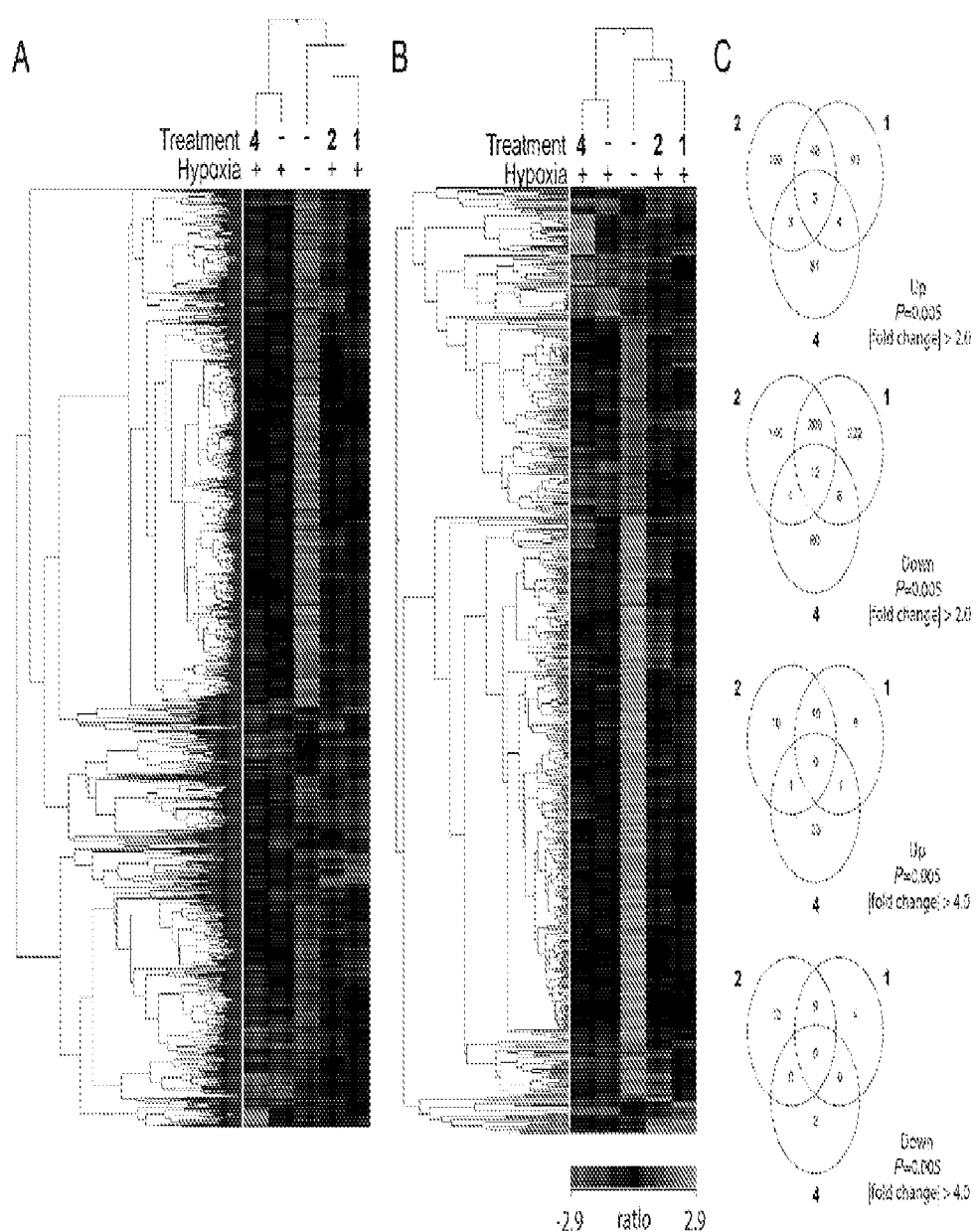

FIG. 12 shows results from gene expression profiling obtained with Affymetrix Human Gene ST 1.0 Arrays. (A) Agglomerative hierarchical clustering of expression changes of the 3328 transcripts induced or repressed 2-fold or more (one-way ANOVA, P<0.005) under hypoxia mimicked with GasPak EZ pouch and the four specified conditions: -, no treatment; 1, OOP 1 (10 iuM); 2, OOP 2 (10 μM), 4, OOP 4 (10 μM). Clustering was based on a Pearson centered correlation of intensity ratios for each treatment compared to hypoxic cells (controls) using average-linkage as a distance. Of this hypoxia-induced set, 148 were induced and 449 were inhibited by OOP 1, whereas 217 were induced and 371 inhibited by OOP 2 (|fold-change|>2.0, P<0.005). Treatment with control OOP 4 induced 91 and inhibited 82 transcripts (|fold-change|>2.0, P<0.005). (B) Clustering of expression changes of the 571 transcripts induced or repressed 4-fold or more (P<0.005) by hypoxia mimicked with GasPak EZ pouch under the designated treatment conditions. Clustering parameters were the same as in (A). All reported treatments are error-weighted averages from three experiments. (C) Venn diagrams representing transcripts down- and up-regulated (|fold-change|>2.0, P<0.005 and |fold-change|>4.0, P<0.005, respectively) by OOP 1 (10 μM), OOP 2 (10 μM), and OOP 4 (10 μM). Numbers inside the intersections represent hypoxia-induced transcripts affected by the treatments.

Figure 13:
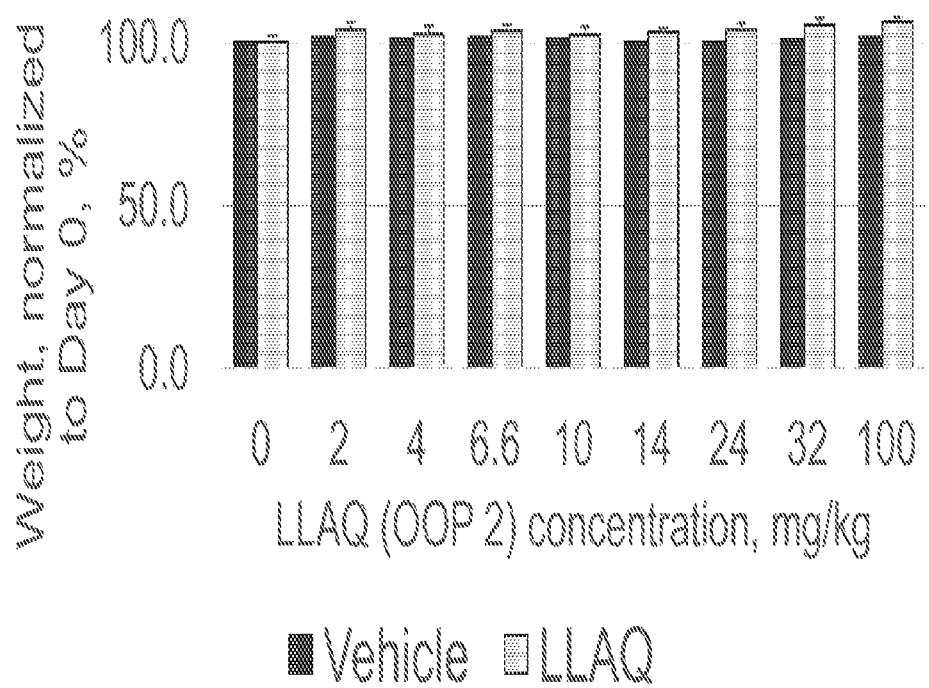

FIG. 13 shows a maximum tolerated dose study using OOPS of the invention.

Figure 14:
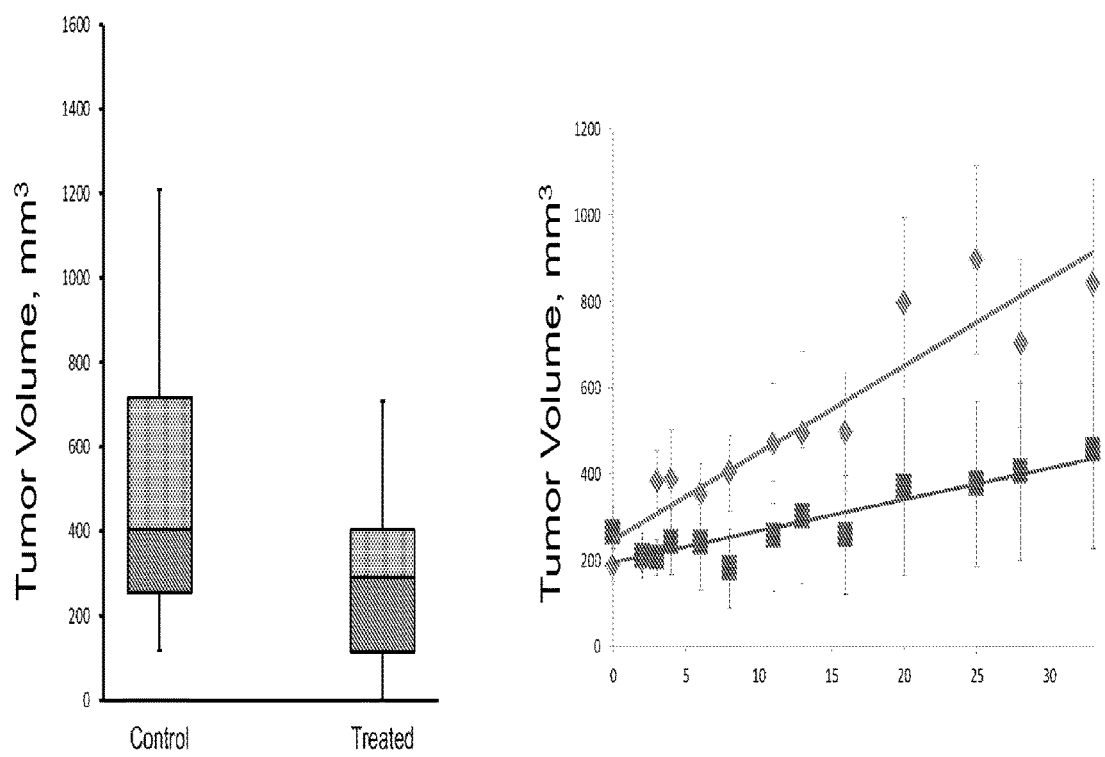

FIG. 14 shows a mouse xenograft study using OOPS of the invention.

DETAILED DESCRIPTION

In some aspects, disclosed herein are novel compounds. For example, such compound may serve as α-helix mimetics, and/or may inhibit protein-protein interactions. Additionally, the present disclosure also provide pharmaceutical compositions or kits comprising compounds described herein and method of treating diseases, for example, diseases resulting from aberrant protein-protein interactions.

In one aspect, the present invention provides a compound of formula I:

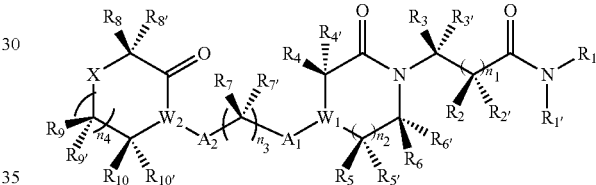

or a pharmaceutically acceptable salt thereof, wherein each of $R_1$ and $R_{1'}$ is independently selected from the group consisting of H, alkyl, cycloalkyl and heteroalkyl or $R_1$, $R_{1'}$ and the N they are attached to in combination form the structure

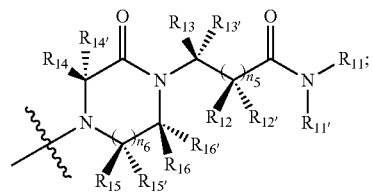

each of $R_{11}$ and $R_{11'}$ is independently selected from the group consisting of H, alkyl, cycloalkyl and heteroalkyl; each of $n_1$, $n_3$ and $n_5$ is independently 0 or 1; each of $n_2$, $n_4$ and $n_6$ is independently 0, 1, 2 or 3; $A_1$-$W_1$ is selected from

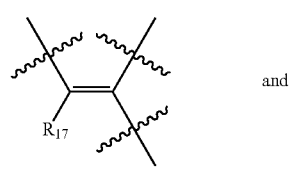

and

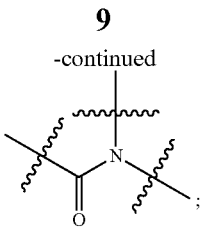

$W_2-A_2$ is selected from

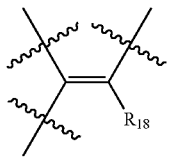 and 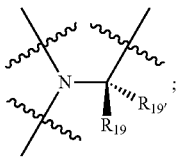 ;

each of $R_2$, $R_{2'}$, $R_3$, $R_{3'}$, $R_4$, $R_{4'}$, $R_5$, $R_{5'}$, $R_6$, $R_{6'}$, $R_7$, $R_{7'}$, $R_8$, $R_{8'}$, $R_9$, $R_{9'}$, $R_{10}$, $R_{10'}$, $R_{12}$, $R_{12'}$, $R_{13}$, $R_{13'}$, $R_{14}$, $R_{14'}$, $R_{15}$, $R_{15'}$, $R_{16}$, $R_{16'}$, $R_{17}$, $R_{18}$, $R_{19}$ and $R_{19'}$ is independently selected from the group consisting of H, alkyl, cycloalkyl, heteroalkyl, alkylamine, alkylhydroxyl, alkylthiol, alkylcarboxylic acid, alkylamide, alkylguanidine, aryl, heteroaryl, alkylaryl, alkylheteroaryl and an amino acid side chain;

X is selected from the group consisting of O, S, S(O), S(O)$_2$, —NR$_{21}$, —NC(=O)R$_{22}$, —NS(=O)$_2$NR$_{23}$R$_{24}$, —NS(=O)$_2$R$_{25}$ and —NC(=O)NR$_{26}$R$_{27}$;

each of $R_{21}$, $R_{22}$, $R_{23}$, $R_{24}$, $R_{25}$, $R_{26}$ and $R_{27}$ is independently selected from the group consisting of H, alkyl, cycloalkyl, heteroalkyl, aryl, heteroaryl, and any pair of $R_{23}/R_{24}$ and $R_{26}/R_{27}$ may optionally form a 5-8 membered, substituted or unsubstituted, saturated or unsaturated, heterocyclic or carbocyclic ring; and when (i) each of $n_2$, $n_4$ and $n_6$ is 1; (ii) each of $n_1$ and $n_3$ is 0; (iii) $A_1-W_1$ is

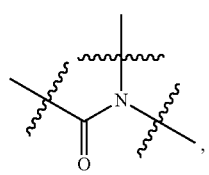 [SMILES: *C(=O)N(*)*] , and (iv) $W_2-A_2$ is

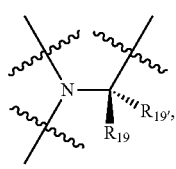

then X is selected from the group consisting of O, S, S(O), S(O)$_2$, —NS(=O)$_2$NR$_{23}$R$_{24}$ and —NS(=O)$_2$R$_{25}$.

In one embodiment, each of $R_1$ and $R_{1'}$ is H and $n_1$ is 0.

In one embodiment, each of $n_2$, $n_4$, and $n_6$ is 1; each of $n_1$, $n_3$ and $n_5$ is 0; and each of $R_5$, $R_{5'}$, $R_6$, $R_{6'}$, $R_9$, $R_{9'}$, $R_{10}$, $R_{10'}$, $R_{15}$, $R_{15'}$, $R_{16}$ and $R_{16'}$ and $R_{32'}$ is H.

In another embodiment, the present invention provides a compound or a pharmaceutically acceptable salt of formula Ia:

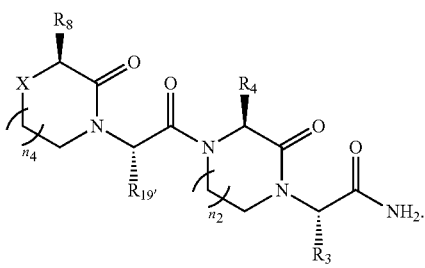

In another embodiment, the present invention provides a compound or a pharmaceutically acceptable salt of formula Ib:

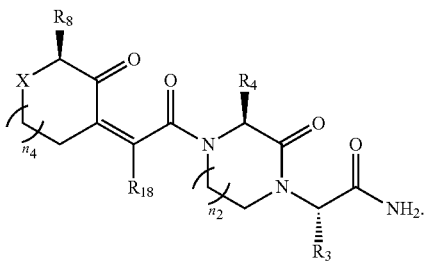

In another embodiment, the present invention provides a compound or a pharmaceutically acceptable salt of formula Ic:

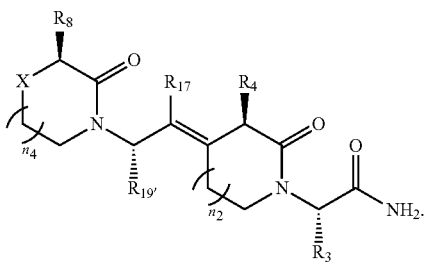

In another embodiment, the present invention provides a compound or a pharmaceutically acceptable salt of formula Id:

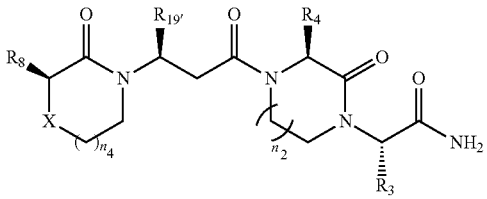

In a further embodiment, each of $n_2$ and $n_4$ in formulas I, Ia, Ib, Ic and Id is 1. In another further embodiment, X in formulas I, Ia, Ib, Ic and Id is O, S or NH.

In another aspect, the present invention provides a compound of formula II:

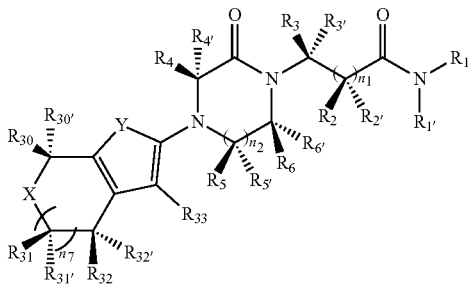

or a pharmaceutically acceptable salt thereof, wherein

Y is selected from the group consisting of O, S and —$NR_{34}$;

each of $R_1$ and $R_{1'}$ is independently selected from the group consisting of H, alkyl, cycloalkyl and heteroalkyl or $R_1$, $R_{1'}$ and the N they are attached to in combination form the structure

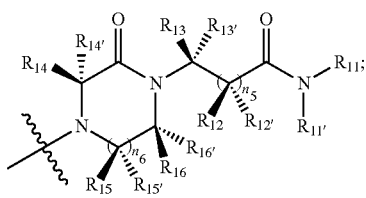

each of $R_{11}$ and $R_{11'}$ is independently selected from the group consisting of H, alkyl, cycloalkyl and heteroalkyl;

each of $n_1$ and $n_5$ is independently 0 or 1;

each of $n_2$ and $n_6$ is independently 1, 2 or 3;

$n_7$ is 0, 1, 2 or 3;

each of $R_2$, $R_{2'}$, $R_3$, $R_{3'}$, $R_4$, $R_{4'}$, $R_5$, $R_{5'}$, $R_6$, $R_{6'}$, $R_{12}$, $R_{12'}$, $R_{13}$, $R_{13'}$, $R_{14}$, $R_{14'}$, $R_{15}$, $R_{15'}$, $R_{16}$, $R_{16'}$, $R_{30}$, $R_{30'}$, $R_{31}$, $R_{31'}$, $R_{32}$, $R_{32'}$ and $R_{34}$ is independently selected from the group consisting of H, alkyl, cycloalkyl, heteroalkyl, alkylamine, alkylhydroxy, alkylthiol, alkylcarboxylic acid, alkyl amide, alkylguanidine, aryl, heteroaryl, alkylaryl, alkylheteroaryl and an amino acid side chain; $R_{33}$ is selected from the group consisting of H, —$NO_2$, —$OCF_3$, —CN, alkyl, cycloalkyl, amino, hydroxyl, halogen, aryl, heteroaryl, alkylamine, alkylhydroxy, alkylthiol, alkylcarboxylic acid, alkylamide, alkylguanidine, aryl, heteroaryl, alkylaryl and alkylheteroaryl;

X is selected from the group consisting of O, S, S(O), S(O)$_2$, —$NR_{21}$, —NC(=O)$R_{22}$, —NS(=O)$_2NR_{23}R_{24}$, —NS(=O)$_2R_{25}$, and —NC(=O)$NR_{26}R_{27}$; and each of $R_{21}$, $R_{22}$, $R_{23}$, $R_{24}$, $R_{25}$, $R_{26}$ and $R_{27}$ is independently selected from the group consisting of H, alkyl, cycloalkyl, heteroalkyl, aryl, heteroaryl, and any pair of $R_{23}/R_{24}$ and $R_{26}/R_{27}$ may optionally form a 5-8 membered, substituted or unsubstituted, saturated or unsaturated, heterocyclic or carbocyclic ring.

In one embodiment, each of $R_1$ and $R_{1'}$ is H and $n_1$ is 0.

In one embodiment, each of $n_1$ and $n_5$ is 0; each of $n_2$, $n_6$ and $n_7$ is 1; and each of $R_5$, $R_{5'}$, $R_6$, $R_{6'}$, $R_{15}$, $R_{15'}$, $R_{16}$, $R_{16'}$, $R_{31}$, $R_{31'}$, $R_{32}$ and $R_{32'}$ is H.

In another aspect, the present invention provides a compound or a pharmaceutically acceptable salt of formula IIa:

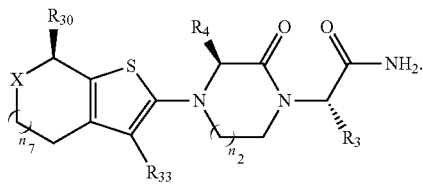

In a further embodiment, each of $n_2$ and $n_4$ in formulas II and IIa is 1. In another further embodiment, X in formulas II and IIa is O, S or NH.

In another aspect, is the present invention provides a compound of formula III:

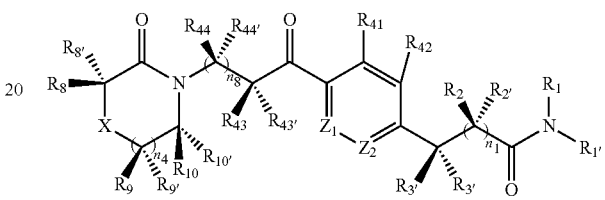

or a pharmaceutically acceptable salt thereof, wherein each of $R_1$ and $R_{1'}$ is independently selected from the group consisting of H, alkyl, cycloalkyl and heteroalkyl or $R_1$, $R_{1'}$ and the N they are attached to in combination form the structure

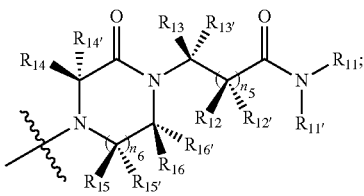

each of $R_{11}$ and $R_{11'}$ is independently selected from the group consisting of H, alkyl, cycloalkyl and heteroalkyl;

each of $Z_1$ and $Z_2$ is independently N or —$CR_{45}$;

each of $R_{41}$, $R_{42}$ and $R_{45}$ is independently selected from the group consisting of H, —$NO_2$, —$OCF_3$, —CN, alkyl, cycloalkyl, amino, hydroxyl, halogen, aryl, heteroaryl, alkylamine, alkylhydroxy, alkylthiol, alkylcarboxylic acid, alkylamide, alkylguanidine, aryl, heteroaryl, alkylaryl and alkylheteroaryl;

each of $R_2$, $R_{2'}$, $R_3$, $R_{3'}$, $R_8$, $R_{8'}$, $R_9$, $R_{9'}$, $R_{10}$, $R_{10'}$, $R_{12}$, $R_{12'}$, $R_{13}$, $R_{13'}$, $R_{14}$, $R_{14'}$, $R_{15}$, $R_{15'}$, $R_{16}$, $R_{16'}$, $R_{43}$, $R_{43'}$, $R_{44}$ and $R_{44'}$ is independently selected from the group consisting of H, alkyl, cycloalkyl, heteroalkyl, alkylamine, alkylhydroxy, alkylthiol, alkylcarboxylic acid, alkyl amide, alkylguanidine, aryl, heteroaryl, alkylaryl, alkylheteroaryl and an amino acid side chain;

each of $n_1$, $n_5$ and $n_8$ is independently 0 or 1;

each of $n_4$ and $n_6$ is independently 1, 2 or 3;

X is selected from the group consisting of O, S, S(O), S(O)$_2$, —$NR_{21}$, —NC(=O)$R_{22}$, —NS(=O)$_2NR_{23}R_{24}$, —NS(=O)$_2R_{25}$, and —NC(=O)$NR_{26}R_{27}$; and each of $R_{21}$, $R_{22}$, $R_{23}$, $R_{24}$, $R_{25}$, $R_{26}$ and $R_{27}$ is independently selected from the group consisting of H, alkyl, cycloalkyl, heteroalkyl, aryl, heteroaryl, and any pair of $R_{23}/R_{24}$ and $R_{26}/R_{27}$ may optionally form a 5-8 membered, substituted or unsubstituted, saturated or unsaturated, heterocyclic or carbocyclic ring.

In one embodiment, each of $R_1$ and $R_{1'}$ is H and $n_1$ is 0.

In one embodiment, each of $n_1$, $n_5$ and $n_8$ is 0; each of $n_4$ and $n_6$ is 1; and each of $R_9$, $R_{9'}$, $R_{10}$, $R_{10'}$, $R_{15}$, $R_{15'}$, $R_{16}$ and $R_{16'}$ is H.

In another embodiment, the present invention provides a compound or pharmaceutically acceptable salt of formula IIIa:

In a further embodiment, $n_4$ in formula IIIa is 1. In another further embodiment, X in formula IIa is 0, S or NH.

In yet another aspect, the present invention provides a compound of formula IV:

or a pharmaceutically acceptable salt thereof, wherein
each of $R_1$ and $R_{1'}$ is independently selected from the group consisting of H, alkyl, cycloalkyl and heteroalkyl or $R_1$, $R_{1'}$ and the N they are attached to in combination form the structure each of $R_{11}$ and $R_{11'}$ is independently selected from the group consisting of H, alkyl, cycloalkyl and heteroalkyl;
$Z_3$ is N or —$CR_{54}$;
$Z_4$ is N or —$CR_{55}$;
$Z_5$ is N or —$CR_{56}$;
each of $R_{52}$, $R_{53}$, $R_{54}$, $R_{55}$ and $R_{56}$ is independently selected from the group consisting of H, —$NO_2$, —CN, —$OCF_3$, alkyl, cycloalkyl, amino, hydroxyl, halogen, aryl, heteroaryl, alkylamine, alkylhydroxy, alkylthiol, alkylcarboxylic acid, alkyl amide, alkylguanidine, aryl, heteroaryl, alkylaryl, and alkylheteroaryl;
each of $n_1$, $n_3$ and $n_5$ is independently 0 or 1;
each of $n_2$ and $n_6$ is independently 1, 2 or 3;
$A_1$-$W_1$ is selected from and
each of $R_2$, $R_{2'}$, $R_3$, $R_{3'}$, $R_4$, $R_{4'}$, $R_5$, $R_{5'}$, $R_6$, $R_{6'}$, $R_7$, $R_{7'}$, $R_{12}$, $R_{12'}$, $R_{13}$, $R_{13'}$, $R_{14}$, $R_{14'}$, $R_{15}$, $R_{15'}$, $R_{16}$, $R_{16'}$, $R_{17}$, $R_{51}$ and $R_{51'}$ is independently selected from the group consisting of H, alkyl, cycloalkyl, heteroalkyl, alkylamine, alkylhydroxy, alkylthiol, alkylcarboxylic acid, alkyl amide, alkylguanidine, aryl, heteroaryl, alkylaryl, alkylheteroaryl and an amino acid side chain.

In one embodiment, each of $R_1$ and $R_{1'}$ is H and $n_1$ is 0.

In one embodiment, each of $n_1$, $n_3$ and $n_5$ is 0; each of $n_2$ and $n_6$ is 1; and each of $R_5$, $R_{5'}$, $R_6$, $R_{6'}$, $R_{15}$, $R_{15'}$, $R_{16}$ and $R_{16'}$ is H.

In another embodiment, the present invention provides a compound or pharmaceutically acceptable salt of formula IVa:

In a further embodiment, $n_2$ in formula IVa is 1. In another further embodiment, $Z_3$ in formula IVa is CH or N.

X-ray crystallographic structures of a variety of protein-protein complexes are available from Protein Data Bank (http://www.rcsb.org/pdb/home/home.do). In addition, system for generating databases of protein secondary structures involved inter-chain protein interactions has been described (US 2010/0281003 to Jochim and Arora, published on Nov. 4, 2010, and incorporated herein by reference). Based on available information, novel compounds according to formulas I, Ia, Ib, Ic, Id, II, IIa, III, IIIa, IV and IVa with specific side chains to target a particular protein-protein interaction are designed. In some embodiments, the design is based on at least one α-helix involved in the protein-protein interaction. In a further embodiment, the side chains attached to formulas I, Ia, Ib, Ic, Id, II, IIa, III, IIIa, IV and IVa mimic the i, i+4, i+7 residues involved in binding. Without being limiting, exemplary compounds of formulas I, Ia, Ib, Ic, Id, II, IIa, III, IIIa, IV and IVa, along with their protein targets, are shown in Table 1.

TABLE 1

Exemplary Compounds and Their Helical Targets

| Target | Substituents | | | | | | | | | | | |
|---|---|---|---|---|---|---|---|---|---|---|---|---|
| | $R_8$ | $R_{8'}$ | $R_{19}$ | $R_{19'}$ | $R_4$ | $R_{4'}$ | $R_3$ | $R_{3'}$ | $R_{14}$ | $R_{14'}$ | $R_{13}$ | $R_{13'}$ |
| HDM2 Trimer | —CH₂Ph | H | H | (1H-indol-3-yl)methyl | isobutyl | H | isobutyl | H | isobutyl | H | —CH₃ | H |
| HDM2 Dimer | —CH₂Ph | H | H | (1H-indol-3-yl)methyl | isobutyl | H | isobutyl | H | | | | |
| p300-TAZ1 Dimer B | isobutyl | H | H | isobutyl | —CH₃ | H | —CH₂CH₂C(O)NH₂ | H | | | | |
| p300-KIX Dimer C | isobutyl | H | H | isobutyl | isobutyl | H | —CH(OH)CH₂CH₃ | H | | | | |

TABLE 1-continued

Exemplary Compounds and Their Helical Targets

| Target | Substituents | | | | | | | | | | |
|---|---|---|---|---|---|---|---|---|---|---|---|
| | R$_8$ | R$_{8'}$ | R$_{19}$ | R$_{19'}$ | R$_4$ | R$_{4'}$ | R$_3$ | R$_{3'}$ | R$_{14}$ | R$_{14'}$ | R$_{13}$ | R$_{13'}$ |
| p300-SID Dimer C | (CH$_2$)$_3$NHC(=NH)NH$_2$ | H | H | isobutyl | isobutyl | H | isobutyl | H | | | |
| P300-Ibid Dimer C | (CH$_2$)$_2$COOH | H | H | CH$_2$CH$_2$SCH$_3$ | —CH$_3$ | H | t-butyl | H | | | |
| P53/MDM2 Trimer | —CH$_2$Ph | H | H | indol-3-ylmethyl | (CH$_2$)$_4$NH | H | isobutyl | H | isobutyl | H | |

TABLE 1-continued

Exemplary Compounds and Their Helical Targets

| Target | Substituents | | | | | | | | | | |
|---|---|---|---|---|---|---|---|---|---|---|---|
| | R₈ | R₈' | R₁₉ | R₁₉' | R₄ | R₄' | R₃ | R₃' | R₁₄ | R₁₄' | R₁₃ | R₁₃' |
| P53/MDM2 Dimer A | —CH₂Ph | H | H | 3-indolyl-CH< | (CH₂)₄NH₂ | H | isobutyl | H | | | |
| Hif1/p300 Dimer B | isobutyl | H | H | isobutyl | —CH₃ | H | —(CH₂)₂C(O)NH₂ | H | | | |
| cMyb/KIX Dimer C | isobutyl | H | H | isobutyl | isobutyl | H | CH(OH)CH₂CH₃ | H | | | |

In some embodiments, compounds of the inventions ("OOPs") include the following structures:

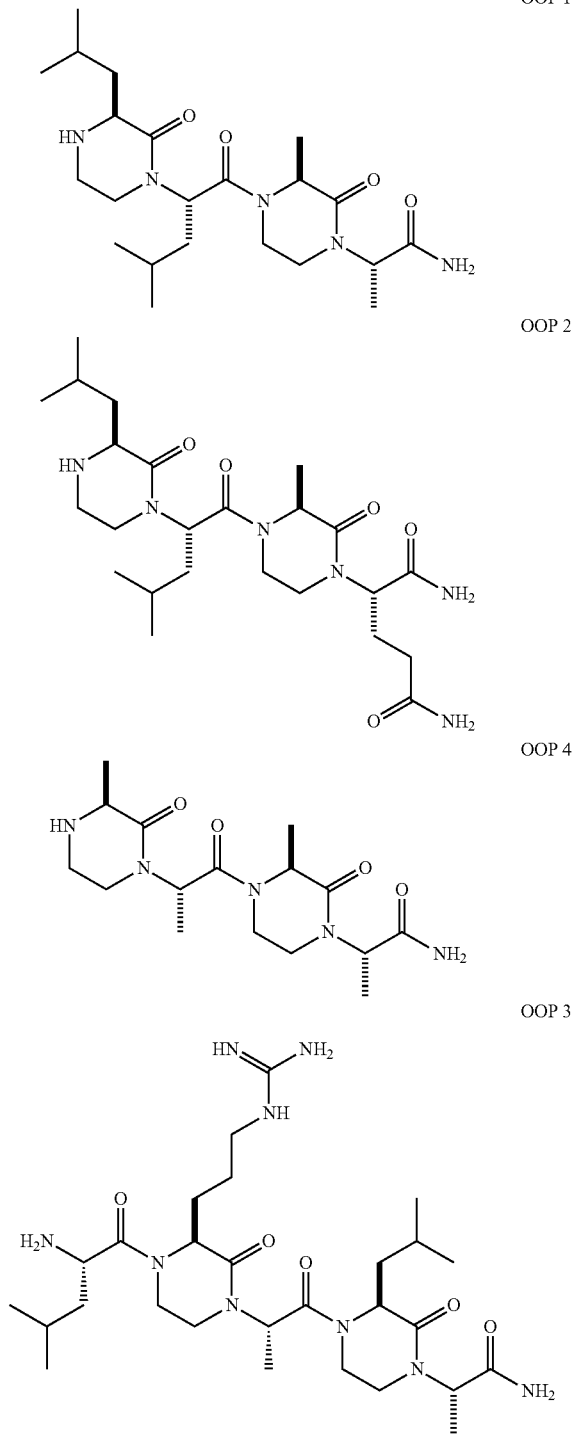

DEFINITIONS

As used herein, the term "alkyl" means an aliphatic hydrocarbon group which may be straight or branched having 1 to 10 carbon atoms in the chain. Branched means that one or more alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl. The alkyl group may optionally substituted with one or more halogen atoms, for example, $CF_3$ and $—CH_2CFH_2$.

As used herein, the term "cycloalkyl" refers to a non-aromatic saturated or unsaturated mono- or polycyclic ring system which may contain 3 to 12 carbon atoms, and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane. The cycloalkyl group may optionally substituted with one or more halogen atoms.

The term "alkenyl" refers to a straight or branched hydrocarbon chain radical group consisting solely of carbon and hydrogen atoms, containing at least one double bond, and having from two to ten carbon atoms (i.e. $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. The alkenyl is unsubstituted or substituted.

The term "heterocycle," by itself or in combination with another term, means, unless otherwise stated, a cyclic non-aromatic hydrocarbon radical, consisting of at least one carbon atom and at least one heteroatom selected from the group consisting of O, N, P, Si and S, and wherein the heteroatom(s) is part of the ring structure and the nitrogen, phosphorus, and sulfur atoms may optionally be oxidized and the nitrogen heteroatom may optionally be quaternized. Examples include, but are not limited to,

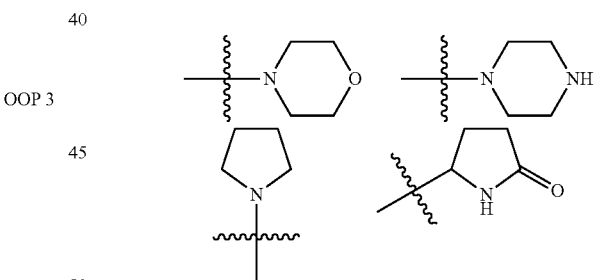

The term "heteroalkyl," by itself or in combination with another term, means, unless otherwise stated, a straight or branched chain, or cyclic hydrocarbon radical, or combinations thereof, consisting of at least one carbon atom and at least one heteroatom selected from the group consisting of O, N, P, Si and S, and wherein the heteroatom(s) is placed at the interior position and the nitrogen, phosphorus, and sulfur atoms may optionally be oxidized and the nitrogen heteroatom may optionally be quaternized. The alkyl portion of the moiety is unsubstituted or substituted. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2—S—CH_3$, $—CH_2—CH_2—S(O)—CH_3$, $—CH_2—CH_2—S(O)_2—CH_3$, $—Si(CH_3)_3$, and $—CH_2—O—CH_3$. Up to two or three heteroatoms may be consecutive, such as, for example, —CH₂—NH—OCH₃ and —CH₂—O—Si(CH₃)₃. In the case of a cyclic hydrocarbon radical, heteroatoms are not part of the ring structure.

The term "heteroalkenyl," by itself or in combination with another term, means, unless otherwise stated, a straight or branched chain, or cyclic hydrocarbon radical, or combinations thereof, consisting of at least two carbon atoms and at least one heteroatom selected from the group consisting of O, N, P, Si and S, and wherein the heteroatom(s) is placed at the interior position and the nitrogen, phosphorus, and sulfur atoms may optionally be oxidized and the nitrogen heteroatom may optionally be quaternized. The alkenyl portion of the moiety is unsubstituted or substituted. Examples include, but are not limited to, —CH=CH—CH₂—O—CH₃, —CH=CH—CH₂—NH—CH₃, —CH=CH—CH₂—N(CH₃)—CH₃, and —CH=CH—CH₂—CH₂—S(O)₂CH₃. Up to two or three heteroatoms may be consecutive.

The term "amino" refers to —NR'R", wherein R' and R" is independently selected from H, alkyl, cycloalkyl, aryl, heteroaryl, heteroalkyl and heteroalkenyl. Examples include, but are not limited to, —NH₂, NHCH₃, —N(CH₃)₂, —NHC₆H₆ and —N(CH₃)C₆H₆.

The term "alkoxyl" refers to —OR', wherein R' is selected from H, alkyl, cycloalkyl, heteroalkyl and heteroalkenyl. Examples include, but are not limited to —OCH₃, —OCF₃, —OCH₂CH₃ and —OCH(CH₃)₂.

The term "alkylhydroxyl" refers to a branched or linear alkyl group wherein at least one termini is substituted with a hydroxyl group. Examples include, but are not limited to, —CH₂OH, —CH₂CH₂OH, —CH₂—CH(CH₂CH₂OH)₂ and —CH₂CH₂CH₂OH.

The term "alkylthiol" refers to a branched or linear alkyl group wherein at least one termini is substituted with a —SH group. Examples include, but are not limited to, —CH₂SH, —CH₂CH₂SH and —CH₂CH₂CH₂SH.

The term "alkylcarboxylic acid" refers to a branched or linear alkyl group wherein at least one termini is substituted with a —COOH group. Examples include, but are not limited to, —CH₂COOH, —CH₂CH₂COOH and —CH₂CH₂CH₂COOH.

The term "alkylamide" refers to a branched or linear alkyl group wherein at least one termini is substituted with a —CONR'R" group, wherein R' and R" is independently selected from H, alkyl, cycloalkyl, aryl, heteroaryl, heteroalkyl and heteroalkenyl. Examples include, but are not limited to, —CH₂CONH₂, —CH₂CH₂CONH₂ and —CH₂CH₂CONHCH₃.

The term "alkylamine" refers to a branched or linear alkyl group wherein at least one termini is substituted with a —NR'R" group, wherein R' and R" is independently selected from H, alkyl, cycloalkyl, aryl, heteroaryl, heteroalkyl and heteroalkenyl. Examples include, but are not limited to, —NH₂, —NHCH₃, —CH₂NHCH₃ and —CH₂CH₂NHCH₃.

The term "alkylguanidine" refers to a branched or linear alkyl group wherein at least one termini is substituted or unsubstituted guanidine group. Examples include, but are not limited to,

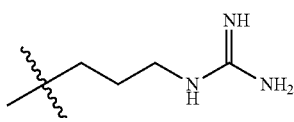

-continued

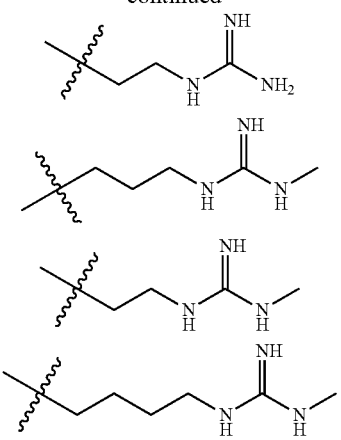

The term "aryl" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl) phenyl, and 2-iodo-4-methylphenyl. An aryl moiety is unsubstituted or substituted.

The term "alkylaryl" refers to a branched or linear alkyl group wherein at least one termini is substituted with an aryl group. Examples include, but are not limited to,

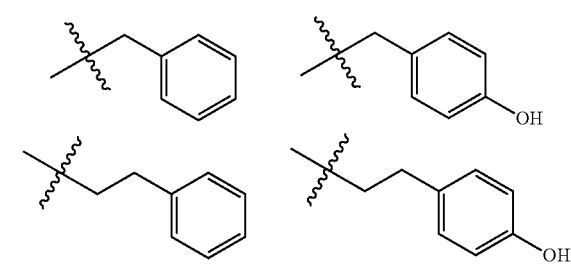

The term "alkylheteroaryl" refers to a branched or linear alkyl group wherein at least one termini is substituted with a heteroaryl group. Examples include, but are not limited to,

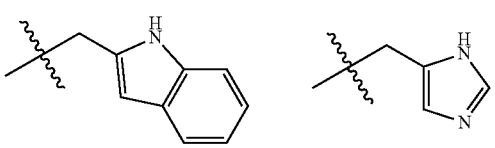

-continued

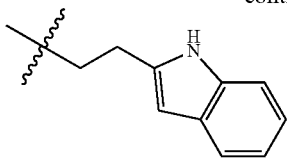 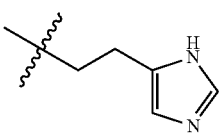

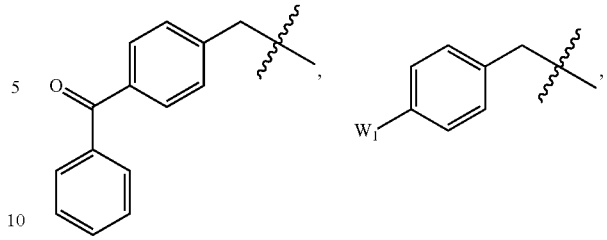

The term "halogen" refers to Cl, Br, I and F.

As used herein, the term "heteroaryl" refers to an aromatic ring radical which comprises at least two carbon atoms and from one to five heteroatoms selected from the group consisting of nitrogen, oxygen, and sulfur. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl and benzimidazolyl.

As used herein, an "amino acid" may be a natural or an unnatural amino acid. Natural amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Examples of unnatural amino acids include enantiomers of natural amino acids, racemic mixtures of natural amino acids, and homologs of any one of the following; (i) natural amino acids; (ii) enantiomers of natural amino acids; and (iii) racemic mixtures of natural amino acids. Additionally, unnatural amino acids include those represented by the following formula V:

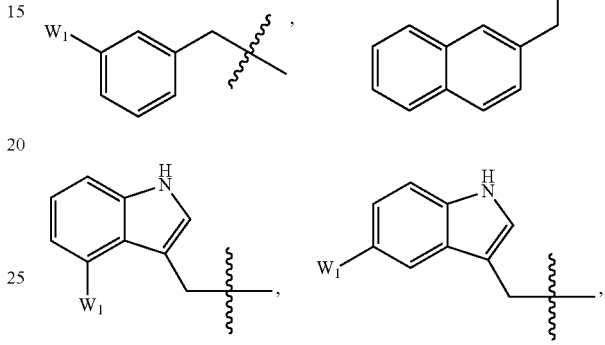

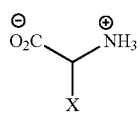

wherein X is selected from the group consisting of

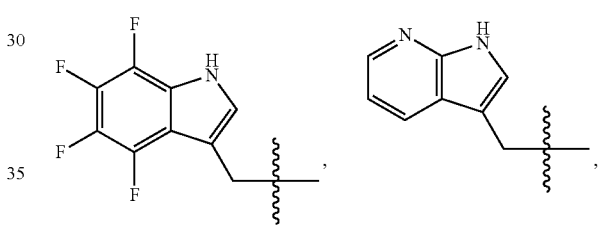

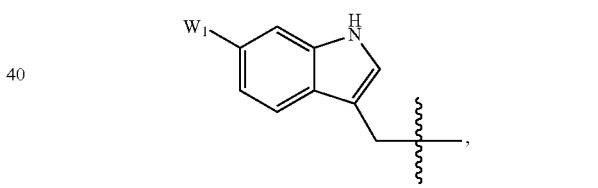

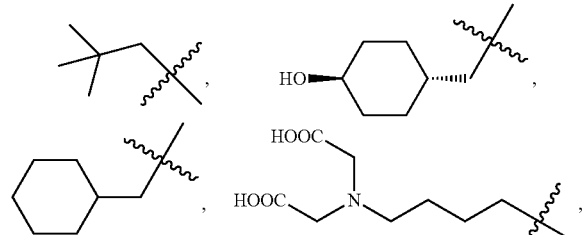

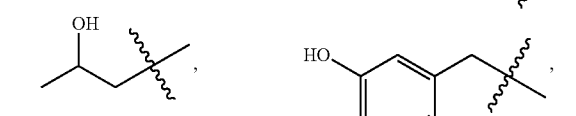

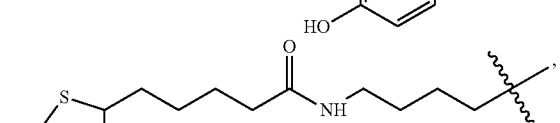

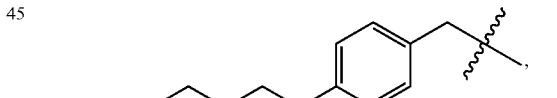

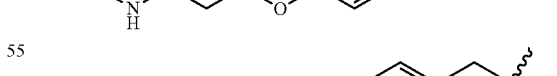

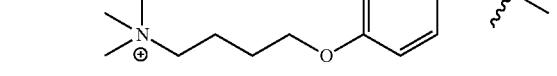

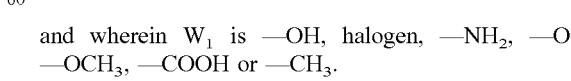

and wherein $W_1$ is —OH, halogen, —$NH_2$, —$OCF_3$, —$OCH_3$, —COOH or —$CH_3$.

As used herein, the term "homolog" refers to two compounds which are differed by one or more $CH_2$ unit. For example, both of the structure shown below are homologs of racemic tryptophan:

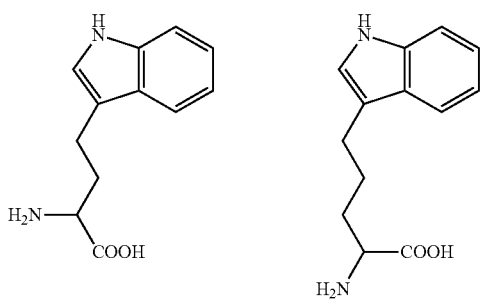 [SMILES: NC(CCc1c[nH]c2ccccc12)C(=O)O ; NC(CCCc1c[nH]c2ccccc12)C(=O)O]

The term "neoplastic disease" or "neoplasm" generally refers to an abnormal mass of tissue as a result of an abnormal proliferation of cells. Neoplasms and/or neoplastic diseases include, e.g., tumors, cancers, carcinomas, metastases, or any disease or disorder characterized by uncontrolled cell growth.

Pharmaceutical Compositions

Another aspect of the present invention relates to pharmaceutical formulations comprising any of the above described heterocyclic compounds formulas I, Ia, Ib, Ic, Id, II, IIa, III, IIIa, IV or a pharmaceutically acceptable salt of formulas I, Ia, Ib, Ic, Id, II, IIa, III, IIIa, IV and IVa, and a pharmaceutically acceptable carrier. Pharmaceutically acceptable salts as used herein include but are not limited to salts of acidic or basic groups. The compounds included in the present compositions that are basic in nature are capable of forming a wide variety of salts with various inorganic and organic acids. The acids that may be used to prepare pharmaceutically acceptable acid addition salts of such compounds are those that form non-toxic acid addition salts, i.e. salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, mesylate, hydroxyethyl sulfonate, and pamoate (i.e., 1,1'-methylene-bis-(2-hydroxy-3-naphthoate)) salts. The compounds included in the present compositions that include an amino moiety may form pharmaceutically acceptable salts with various amino acids, in addition to the acids mentioned above. Compounds included in the present compositions that are acidic in nature are capable of forming base salts with various pharmacologically or cosmetically acceptable cations, examples of which include, e.g., alkali metal or alkaline earth metal salts and, particularly, calcium, magnesium, sodium lithium, zinc, potassium, and iron salts.

Pharmaceutically acceptable carriers include all such carriers known to those skilled in the art to be suitable for the particular mode of administration, such as, by way of non-limiting example only, solutions, suspensions, emulsions, excipients, powders, or stabilizers. The carrier should be suitable for the desired mode of delivery. A pharmaceutically acceptable carrier for the present compositions can include, but are not limited to, amino acids, biological polymers, peptides, non-biological polymers, sugars or starches, inorganic salts, and gums, which may be present singly or in combinations thereof. Non-limiting examples of peptides used in the acceptable carrier include, e.g., gelatin, albumin. In some embodiments, cellulose or its derivatives may be used in the pharmaceutically acceptable carrier. Non-limiting examples of sugars used the acceptable carrier include, e.g., lactose, glucose, fructose, galactose, lacticol, maltitol, maltose, mannitol, melezitose, myoinositol, palatinate, raffinose, stachyose, sucrose, tehalose, xylitol, hydrates thereof, and combinations of thereof. In some embodiments, binders may be included in the pharmaceutically acceptable carrier. Examples of binders include, but are not limited to, starches (for example, corn starch or potato starch), gelatin; natural or synthetic gums such as acacia, sodium alginate, powdered tragacanth, cellulose, guar gum or cellulose derivatives (for example, methycellulose, ethyl cellulose, cellulose acetate); microcrystalline cellulose, polyvinyl pyrrolidone, and mixtures thereof. In some embodiments, the inorganic salts used in the acceptable carrier may be a magnesium salt, for example, magnesium chloride or magnesium sulfate. In some embodiments, other inorganic salts may be used, for example, calcium salts. Examples of calcium salts include, but are not limited to, calcium chloride, calcium sulfate. Other examples of substances which may be used in the pharmaceutically acceptable carrier may include, but are not limited to, vegetable oils, such as peanut oil, cottonseed oil, olive oil, corn oil; polyols such as glycerin, propylene glycol, polyethylene glycol; pyrogen-free water, isotonic saline, phosphate buffer solutions; diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Non-limiting examples of lubricants that may be used in the pharmaceutical composition include, e.g., agar, calcium stearate, magnesium stearate, light mineral oil, polyethylene glycol, glycerin, sorbitol, mannitol, other glycols, stearic acid, sodium lauryl sulfate, mineral oil, talc, hydrogenated vegetable oil (e.g., peanut oil, cottonseed oil, sunflower oil, sesame oil, olive oil, corn oil, and soybean oil), zinc stearate, ethyl oleate, ethylaureate, syloid silica gel, coagulated aerosol of synthetic silica, or mixtures thereof.

In some embodiments, the composition may include one or more pharmaceutically acceptable additives, non-limiting examples of which include, e.g., anti-foaming agents, buffering agents, detackifiers, antioxidants, polymers, preservatives, odorants, opacifiers, chelating agents, suspending agents, fillers, plasticizers, and mixtures thereof.

In some embodiments, the pharmaceutically acceptable carrier comprises more than 90%, more than 80%, more than 70%, more than 60%, more than 50%, more than 40%, more than 30%, more than 20%, more than 10%, more than 9%, more than 8%, more than 6%, more than 5%, more than 4%, more than 3%, more than 2%, more than 1%, more than 0.5%, more than 0.4%, more than 0.3%, more than 0.2%, more than 0.1%, more than 0.09%, more than 0.08%, more than 0.07%, more than 0.06%, more than 0.05%, more than 0.04%, more than 0.03%, more than 0.02%, more than 0.01%, more than 0.009%, more than 0.008%, more than 0.007%, more than 0.006%, more than 0.005%, more than 0.004%, more than 0.003%, more than 0.002%, more than 0.001%, more than 0.0009%, more than 0.0008%, more than 0.0007%, more than 0.0006%, more than 0.0005%, more than 0.0004%, more than 0.0003%, more than 0.0002%, or more than 0.0001% of the pharmaceutical composition by w/w, w/v or v/v.

In some embodiments, the concentration of the compound or a pharmaceutically acceptable salt of Formulas I, Ia, Ib, Ic, Id, II, IIa, III, IIIa, IV and IVa comprises less than 100%, less than 90%, less than 80%, less than 70%, less than 60%, less than 50%, less than 40%, less than 30%, less than 20%, less than 10%, less than 9%, less than 8%, less than 6%, less than 5%, less than 4%, less than 3%, less than 2%, less than 1%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, less than 0.01%, less than 0.009%, less than 0.008%, less than 0.007%, less than 0.006%, less than 0.005%, less than 0.004%, less than 0.003%, less than 0.002%, less than 0.001%, less than 0.0009%, less than 0.0008%, less than 0.0007%, less than 0.0006%, less than 0.0005%, less than 0.0004%, less than 0.0003%, less than 0.0002%, or less than 0.0001% of the pharmaceutical composition by w/w, w/v or v/v.

In some embodiments, the pharmaceutical composition is formulated for oral administration. In some embodiments, the pharmaceutical composition is a solid pharmaceutical composition. In some embodiments, the solid pharmaceutical composition is formulated as an oral dosage form. Non-limiting examples of discrete oral dosage forms include tablets, capsules, caplets, gelatin capsules, sustained release formulations, lozenges, thin films, lollipops, chewing gum. In some embodiments, the oral dosage form is coated by known techniques to delay or prolong absorption in the gastrointestinal tract, thus providing a sustained action of a longer period of time.

Examples of lubricants include magnesium stearate, sodium lauryl sulphate, talc, as well as high molecular weight polyethylene glycols.

In other embodiments, the pharmaceutical composition for oral administration is a liquid pharmaceutical composition. Non-limiting examples of liquid compositions for oral administration include, e.g., hydrophilic suspensions, emulsions, liquids, gels, syrups, slurries, solutions, elixirs, softgels, tinctures, hydrogels.

Such dosage forms may be prepared by methods well known to those skilled in the art, e.g., in a pharmacy. Such methods would comprise bringing the compounds of the present invention into association with the pharmaceutically acceptable carrier.

In some embodiments, the pharmaceutical compositions of the present invention are formulated for parenteral administration. "Parenteral administration" refers to routes of administration other than the gastro-intestinal tract. Examples of parenteral administration include, but are not limited to, intravenous injection, subcutaneous injection, intramuscular injection, infusion, or implantation. In some embodiments, infusion may be intradermal, or subcutaneous, or through a transdermal implant. In some cases, infusion may be intracerebral, intracerebrovascular, or epidural. Pharmaceutical compositions for parenteral administration are well known in the art. Examples of the compositions for parenteral administration are disclosed in the following references which are hereby incorporated by reference: US 2006/0287221, U.S. Pat. No. 4,309,421, U.S. Pat. No. 5,244,925, U.S. Pat. No. 4,158,707, U.S. Pat. No. 5,164,405).

In some embodiments, compositions formulated for parenteral administration include aqueous solutions and/or buffers commonly used for injection and/or infusion. Commonly used aqueous buffers and/or solutions may include, but are not limited to, Acetated ringer's solution, sodium chloride solutions of about 0.9%, phosphate buffers, Lactated Ringer's solution, phosphate buffered saline, citrate buffers, Tris buffers, histidine buffers, HEPES buffers, glycine buffers, N-glycylglycine buffers, among others. Other pharmaceutically acceptable carriers for parenteral administration may include, e.g., ethanol, glycerol, proplylene glycol, cyclodextrin and cyclodextrin derivatives, vegetable oils. In some embodiments, pharmaceutical compositions formulated for injection and/or infusion contain preservatives present in amounts that effectively prevent or reduce microbial contamination or degradation. Various agents, e.g., phenol, m-cresol, benzyl alcohol, parabens, ethyl hydroxybenzoate, bismuth tribromophenate, chlorobutanol, methotrexate, sorbic acid, thimerosol, methyl hydroxybenzoate, bacitracin, propyl hydroxybenzoate, erythromycin, 5-fluorouracil, rifamycin, doxorubicin, mitoxantrone, chlorocresol, benzalkonium chlorides, may be used to prevent or reduce contamination.

In some embodiments, sterile solutions are prepared by incorporating the compound(s) of the present invention in the required amount in the appropriate solvent with various other ingredients as described herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain methods of preparation include but are not limited to vacuum-drying and freeze-drying techniques which yield a powder of the active ingredient plus any additional desired ingredient from a previously sterile-filtered solution thereof.

In some embodiments, the pharmaceutical compositions of the present invention are formulated for transdermal delivery devices ("patches"). Such transdermal patches can be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, U.S. Pat. No. 4,992,445 and U.S. Pat. No. 5,001,139, which are herein incorporated by reference.

In some embodiments, the pharmaceutical compositions are formulated for delivery by inhalation. Compositions for inhalation include solutions and suspensions in pharmaceutically acceptable aqueous or organic solvents, or mixtures thereof, and powders. The liquid or solid compositions may contain suitable pharmaceutically acceptable excipients, non-limiting examples of which are described herein. The compositions may be administered by the oral or nasal respiratory route. In some embodiments, compositions in preferably pharmaceutically acceptable solvents are nebulized by use of inert gases. In some embodiments, nebulized solutions are inhaled directly from the nebulizing device. In other embodiments, the nebulizing device is attached to a face mask tent or intermittent positive pressure breathing machine.

Routes of Delivery

One approach for delivering agents into cells involves the use of liposomes. Basically, this involves providing a liposome which includes agent(s) to be delivered, and then contacting the target cell, tissue, or organ with the liposomes under conditions effective for delivery of the agent into the cell, tissue, or organ.

This liposome delivery system can also be made to accumulate at a target organ, tissue, or cell via active targeting (e.g., by incorporating an antibody or hormone on the surface of the liposomal vehicle). This can be achieved according to known methods.

An alternative approach for delivery of protein- or polypeptide containing agents (e.g., heterocyclic compounds of the present invention containing one or more protein or polypeptide side chains) involves the conjugation of the desired agent to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of agents involves preparation of chimeric agents according to U.S. Pat. No. 5,817,789 to Heartlein et al., which is hereby incorporated by reference in its entirety. The chimeric agent can include a ligand domain and the agent (e.g., a heterocyclic compound of the invention). The ligand domain is specific for receptors located on a target cell. Thus, when the chimeric agent is delivered intravenously or otherwise introduced into blood or lymph, the chimeric agent will adsorb to the targeted cell, and the targeted cell will internalize the chimeric agent.

Compounds of the present invention may be delivered directly to the targeted cell/tissue/organ.

Additionally and/or alternatively, the compounds may be administered to a non-targeted area along with one or more agents that facilitate migration of the compounds to (and/or uptake by) a targeted tissue, organ, or cell. As will be apparent to one of ordinary skill in the art, the compound itself can be modified to facilitate its transport to a target tissue, organ, or cell, including its transport across the blood-brain barrier; and/or to facilitate its uptake by a target cell (e.g., its transport across cell membranes). In a preferred embodiment, the compound of the invention is modified, and/or delivered with an appropriate vehicle, to facilitate its delivery to the nucleus of the target cell (Wender et al., "The Design, Synthesis, and Evaluation of Molecules That Enable or Enhance Cellular Uptake: Peptoid Molecular Transporters," Proc. Nat'l Acad. Sci. USA 97:13003-8 (2000); Roberts, "Buyer's Guide to Protein Transduction Reagents," Scientist 18:42-3 (2004); Joliot & Prochiantz, "Transduction Peptides: From Technology to Physiology," Nat. Cell Biol. 6:189-96 (2004), each of which is hereby incorporated by reference in its entirety). Some example target cells, tissues, and/or organs for the embodiments described above are shown in Table 2.

In vivo administration can be accomplished either via systemic administration to the subject or via targeted administration to affected tissues, organs, and/or cells, as described above. Typically, the therapeutic agent (i.e., a compound of the present invention) will be administered to a patient in a vehicle that delivers the therapeutic agent(s) to the target cell, tissue, or organ. Typically, the therapeutic agent will be administered as a pharmaceutical formulation, such as those described above.

Exemplary routes of administration include, without limitation, orally, topically, transdermally, parenterally, subcutaneously, intravenously, intramuscularly, intraperitoneally, intraventricularly, and intralesionally; by intratracheal inoculation, aspiration, airway instillation, aerosolization, nebulization, intranasal instillation, oral or nasogastric instillation, intraperitoneal injection, intravascular injection, intravenous injection, intra-arterial injection (such as via the pulmonary artery), intramuscular injection, and intrapleural instillation; by application to mucous membranes (such as that of the nose, throat, bronchial tubes, genitals, and/or anus); and by implantation of a sustained release vehicle.

Exemplary delivery devices include, without limitation, nebulizers, atomizers, liposomes (including both active and passive drug delivery techniques) (Wang & Huang, "pH-Sensitive Immunoliposomes Mediate Target-cell-specific Delivery and Controlled Expression of a Foreign Gene in Mouse," Proc. Nat'l Acad. Sci. USA 84:7851-5 (1987); Bangham et al., "Diffusion of Univalent Ions Across the Lamellae of Swollen Phospholipids," J Mol. Biol. 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al.; Wolff et al., "The Use of Monoclonal Anti-Thy1 IgG1 for the Targeting of Liposomes to AKR-A Cells in Vitro and in Vivo," Biochim. Biophys. Acta 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of the compound to the desired organ, tissue, or cells in vivo to effect this aspect of the present invention. Exemplary target organs, tissues, or cells are included in Table 2.

TABLE 2

Example Target Cells/Tissues/Organs

| Desired Effect | Example Target(s) |
|---|---|
| Inhibit transcription of: | |
| adrenomedullin | Pheochromocytoma |
| carbonic anhydrase IX | Tumor cells/tissue, incl. cancer |
| ceruloplasmin | Lymphocytes/lymphatic tissue, inflamed tissue, rheumatoid arthritic tissue |
| chemokine receptor type 4 (CXCR4, fusin, CD1 84) | Tumor cells/tissue, incl. cancer |
| c-Met | Tumor cells/tissue, incl. cancer |
| endothelin-1 | Endothelium |
| enolase 1 | Liver, brain, kidney, spleen, adipose, lung |
| erythropoietin | Liver, kidney |
| glucose transporter 1 | Tumor, incl. cancer |
| glucose transporter 3 | Tumor, incl. cancer |
| hexokinase 1 | Tumor, incl. cancer |
| hexokinase 2 | Tumor, incl. cancer |
| IGF binding protein 1 | Brain, liver |
| IGF binding protein 3 | Brain, liver |
| insulin-like growth factor 2 | Brain, liver |
| lactate dehydrogenase A | Heart |
| lysyl oxidase | Tumor cells/tissue, incl. cancer |
| monoamine oxidase | Tumor cells/tissue, esp. prostate cancer |
| monoamine oxidase | Tumor cells/tissue, esp. prostate cancer |

TABLE 2-continued

Example Target Cells/Tissues/Organs

| Desired Effect | Example Target(s) |
| --- | --- |
| nitric oxide synthase 2 | Vessels, cardiovascular cells/tissue |
| phosphofructokinase | Tumor, incl. cancer |
| phosphoglycerate kinase 1 | Tumor, incl. cancer |
| stromal-derived factor 1 | Tumor cells/tissue, incl. cancer |
| transferrin | Liver |
| triose phosphate isomerase | Tumor, incl. cancer |
| vascular endothelial growth | Tumor cells/tissue, incl. cancer |
| vascular endothelial growth factor receptor FLT-1 | Tumor cells/tissue, incl. cancer |
| vascular endothelial growth factor receptor KDR/Flk-1 | Tumor cells/tissue, incl. cancer |
| Treat or prevent: | |
| retinal ischemia | Retina (eye) |
| pulmonary hypertension | Lungs |
| intrauterine growth | Uterus |
| diabetic retinopathy | Retina (eye) |
| age-related macular | Retina (eye) |
| diabetic macular edema | Retina (eye) |
| Reduce or prevent angiogenesis | Tumor cells/tissue, incl. cancer |
| Reduce or prevent metastasis | Tumor cells/tissue, incl. cancer |
| Decrease cell survival and/or proliferation | Cancerous celE, cells contained in the endothelial vasculature of a tissue that contains |

The amount to be administered will vary depending upon the particular conditions and treatment regimen. The amount/dose required to obtain the desired effect may vary depending on the agent, formulation, cell type, culture conditions (for ex vivo embodiments), the duration for which treatment is desired, and, for in vivo embodiments, the individual to whom the agent is administered.

Effective amounts can be determined empirically by those of skill in the art. For example, this may involve assays in which varying amounts of the compounds of the invention are administered to cells in culture and the concentration effective for obtaining the desired result is calculated. Determination of effective amounts for in vivo administration may also involve in vitro assays in which varying doses of agent are administered to cells in culture and the concentration of agent effective for achieving the desired result is determined in order to calculate the concentration required in vivo. Effective amounts may also be based on in vivo animal studies.

Methods of Treatment

Another aspect of the present invention relates to a method of preventing or treating angiogenesis in a tissue of a subject. The method involves administrating a therapeutic effective amount of a compound or composition of the present disclosure to treat or prevent angiogenesis.

Angiogenesis, the induction of new blood vessels, is critical for normal growth as well as pathogenesis of various disorders. In cancers, angiogenesis accelerates growth of solid tumors and provides a gateway to metastasis via the newly formed vasculature. In contrast, therapeutic angiogenesis is important for reducing the effects of tissue ischemia and preventing organ failure. The process of angiogenesis is tightly controlled by a number of specific mitogens, among which vascular endothelial growth factor (VEGF) and its receptors play a key role. The levels of VEGF are upregulated across a broad range of tumors, and play a causal role in oncogenic signaling. In cells and tissues, transcription of VEGF gene is regulated by hypoxia-inducible factors. Among them, Hypoxia-Inducible Factor 1 ("HIF-1") is the main regulator of oxygen-dependent transcription in a majority of organs and accounts for the increase in expression of hypoxia-inducible genes. HIF-1 consists of an oxygen-sensitive a and a constitutively expressed 13 subunit. Under well-oxygenated conditions, HIF-1α is hydroxylated (Ivan et al., "HIFα Targeted for VHL-mediated Destruction by Proline Hydroxylation: Implications for 02 Sensing," Science 292:464-8 (2001)), ubiquitinated, and degraded by the ubiquitin-proteasome system. Under hypoxia, HIF-1α is stabilized and translocates into the nucleus where heterodimerization with its constitutively expressed binding partner, aryl hydrocarbon receptor nuclear translocator ("ARNT") (Wood et al., "The Role of the Aryl Hydrocarbon Receptor Nuclear Translocator (ARNT) in Hypoxic Induction of Gene Expression," *J Biol. Chem.* 271:15117-23 (1996)) results in binding to a cognate hypoxia response element ("HRE") (Forsythe et al., "Activation of Vascular Endothelial Growth Factor Gene Transcription by Hypoxia-inducible Factor 1," *Mol. Cell. Biol.* 16:4604-13 (1996)). The heterodimer then recruits transcriptional coactivators, p300, CBP, and SRC-1, resulting in the upregulation of the hypoxia¬ inducible genes. Regulation of the activity of hypoxia-inducible factors includes three critical steps: (i) inhibition of hydroxylation of two proline residues to preclude interaction of HIF-1α with pVHL, a part of ubiquitin ligase complex, thereby preventing its proteasomal destruction; (ii) inhibition of hydroxylation of Asn803 by Factor Inhibiting HIF-1α ("FIH") (Lando et al., "FIH-1 Is an Asparaginyl Hydroxylase Enzyme That Regulates the Transcriptional Activity of Hypoxia¬ inducible Factor," *Genes & Develop.* 16:1466-71 (2002)) to enable recruitment of coactivators, which trigger overexpression of hypoxia inducible genes, including genes encoding angiogenic peptides such as VEGF and VEGF receptors VEGFR-1 (Flt-1) and VEGFR-2 (KDR/Flk-1), as well as proteins involved in altered energy metabolism, such as the glucose transporters GLUT1 and GLUT3, and hexokinases 1 and 2 (Forsythe et al., "Activation of Vascular Endothelial Growth Factor Gene Transcription by Hypoxia-inducible Factor 1," *Mol. Cell. Biol.* 16:4604-13 (1996); Okino et al., "Hypoxia-inducible Mammalian Gene Expression Analyzed in Vivo at a TATA-driven Promoter and at an Initiator-driven Promoter," *J. Biol. Chem.* 273:23837-43 (1998)); and (iii) interaction of promoter-bound HIF-1α/1 (3 with coactivator protein p300 (or the homologous CREB binding protein, CBP) leading to upregulation of transcription.

Another aspect of the present invention relates to a method of inhibiting HIF-1α-p300/CBP interaction using the compounds of the present invention. The method involves contacting the protein with a compound of the present invention under conditions effective to inhibit the HIF-1α-p300/CBP interaction, for example with a compound of formulas I, Ia, Ib, Ic, Id, II, IIa, III, IIIa, IV or IVa. In some embodiments, the compound disrupts interaction of HIF-1α and p300/CBP and thereby reduces transcription of the gene.

Genes whose transcription is mediated by interaction of HIF-1α with CBP and/or p300 include B-adrenergic receptor, adenylate kinase 3, adrenomedullin, aldolase A, aldolase C, carbonic anhydrase IX, ceruloplasmin, chemokine receptor type 4 (CXCR4, fusin, CD184), c-Met, endothelin-1, enolase 1, erythropoietin, glucose transporter 1, glucose transporter 3, glyceraldehyde-3-phosphate dehydrogenase, heme oxygenase 1, hexokinase 1, hexokinase 2, IGF binding protein 1, IGF binding protein 3, insulin-like growth factor 2, lactate dehydrogenase A, lysyl oxidase, monoamine oxidase isoform A, monoamine oxidase isoform B, nitric oxide synthase 2, p21, p35srg, phosphofructokinase, phosphoglycerate kinase 1, plasminogen activator inhibitor 1, pyruvate kinase M, stromal-derived factor 1, tranferrin receptor, transferrin, transforming growth factor 13, triose phosphate isomerase 1, vascular endothelial growth factor, vascular endothelial growth factor receptor FLT-1, and vascular endothelial growth factor receptor KDR/Flk-1.

Another aspect of the present invention relates to a method of treating a disorder or disease by inhibiting at least one aberrant protein-protein interaction involved in the disorder. The method involves contacting at least one of the proteins involved in the aberrant protein-protein interaction with a compound under conditions effective to inhibit the aberrant protein-protein interaction and thus treating the disorder, for example with a compound of formulas I, Ia, Ib, Ic, Id, II, IIa, III, IIIa, IV or IVa. In some embodiments, the aberrant protein-protein interaction is the HIF-1α-p300/CBP interaction. Representative disorders and gene transcriptions involved are shown in Table 3.

TABLE 3

Example Disorders

| Gene | Treat/prevent |
|---|---|
| adrenomedullin | Pheochromocytoma |
| carbonic anhydrase IX | Cancer |
| ceruloplasmin | Lymphoma, acute and chronic rheumatoid arthritis |
| chemokine receptor type 4 (CXCR4, | Cancer stem cell migration, inflammation |
| c-Met | Metastasis (tumor, incl. cancer) |
| endothelin-1 | Abnormal vasoconstriction |
| enolase 1 | Hashimoto's encephalopathy, severe |
| erythropoietin | Abnormal oxygen transport |
| glucose transporter 1 | Aerobic glycolysis (Warburg effect) |
| glucose transporter 3 | Aerobic glycolysis (Warburg effect) |
| heme oxygenase I | Abnormal oxygen transport |
| hexokinase 1 | Aerobic glycolysis (Warburg effect) |
| hexokinase 2 | Aerobic glycolysis (Warburg effect) |
| IGF binding protein 1 | Abnormal development and function of |
| IGF binding protein 3 | Abnormal development and function of |
| insulin-like growth factor 2 | Abnormal development and function of |
| lactate dehydrogenase A | Myocardial infarction |
| lysyl oxidase | Metastasis (tumor, esp. breast cancer) |
| monoamine oxidase isoform A | Aggression, depression, cancer, esp. |
| monoamine oxidase isoform B | Aggression, depression, cancer, esp. |
| nitric oxide synthase 2 | Abnormal vasomotor tone |
| phosphofructokinase | Aerobic glycolysis (Warburg effect) |
| phosphoglycerate kinase 1 | Aerobic glycolysis (Warburg effect) |
| stromal-derived factor 1 | Cancer |
| tranferrin receptor | Abnormal iron uptake/metabolism |
| transferrin | Abnormal iron uptake/metabolism |
| triose phosphate isomerase 1 | Aerobic glycolysis (Warburg effect) |
| vascular endothelial growth factor | Angiogenesis (tumor, inch cancer) |
| vascular endothelial growth factor | Angiogenesis (tumor, incl. cancer) |
| vascular endothelial growth factor | Angiogenesis (tumor, inch cancer) |

In some embodiments, the disorder a neoplastic disease. In more particular embodiments, the neoplastic disease is cancer. Non-limiting examples of cancers include, e.g., leukemias such as acute leukemia, acute t-cell leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, or chronic lymphocytic leukemia, polycythemia vera, lymphomas such as Hodgkin's lymphoma, follicular lymphoma or non-Hodgkin's lymphoma, multiple myeloma, Waldenstrom's macroglobulinemia, heavy chain disease, solid tumors, sarcomas, carcinomas and other cancers such as, e.g., fibrosarcoma, myxosarcoma, liposarcoma, chondrosarcoma, osteogenic sarcoma, lymphangiosarcoma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic, carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, craniopharyngioma, ependymoma, pinealoma, hemangioblastoma, acoustic neuroma, oligodendroglioma, meningioma, melanoma, neuroblastoma, retinoblastoma, endometrial cancer, non small cell lung cancer, thymus, brain, lung, squamous cell, skin, eye, intraocular melanoma, oral cavity and oropharyngeal cancer, gastric, stomach, head, neck, kidney, liver, esophageal, testicular, gynecological, thyroid, CNS, PNS, AIDS related AIDS-Related (e.g. Lymphoma and Kaposi's Sarcoma) or Viral-Induced cancer.

In some embodiments, the disease in an autoimmune disease. Autoimmune diseases generally refer to a diseases wherein a subject's cells are attacked by the subject's own immune system. Non-limiting examples of autoimmune diseases include, e.g., Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Strauss syndrome, Cicatricial pemphigoid/benign mucosal pemphigoid, Crohn's disease, Cogans syndrome, Cold agglutinin disease, Congenital heart block, Coxsackie myocarditis, CREST disease, mixed cryoglobulinemia, neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Glomerulonephritis, Goodpasture's syndrome, Granulomatosis with Polyangiitis (GPA), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Insulin-dependent diabetes (type1), Interstitial cystitis, Juvenile arthritis, Type I diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, or III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, Wegener's granulomatosis.

In some embodiments, the disorder is an infectious disease. Infectious diseases, also known as transmissible diseases or communicable diseases, generally refer to diseases or illness resulting from the infection, presence and growth of one or more pathogenic biological agents in a subject. Non-limiting examples of infectious diseases include, e.g., *Acinetobacter* infections, Actinomycosis, African sleeping sickness (African trypanosomiasis), AIDS (Acquired immunodeficiency syndrome), Amebiasis, Anaplasmosis, Anthrax, *Arcanobacterium haemolyticum* infection, Argentine hemorrhagic fever, Ascariasis, Aspergillosis, Astrovirus infection, Babesiosis, *Bacillus cereus* infection, bacterial infections, Bacterial pneumonia, Bacterial vaginosis (BV), *Bacteroides* infection, Balantidiasis, *Baylisascaris* infection, BK virus infection, Black piedra, *Blastocystis hominis* infection, Blastomycosis, Bolivian hemorrhagic fever, *Borrelia* infection, Botulism (and Infant botulism), Brazilian hemorrhagic fever, Brucellosis, *Burkholderia* infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, *Chlamydia, Chlamydophila pneumoniae* infection, Cholera, Chromoblastomycosis, Clonorchiasis, *Clostridium difficile* infection, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Dientamoebiasis, Diphtheria, Diphyllobothriasis, Dracunculiasis, Dysentery, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolopsiasis, Fasciolosis, Fatal familial insomnia (FFI), Filariasis, Food poisoning by *Clostridium perfringens*, Free-living amebic infection, *Fusobacterium* infection, fungal infections, Gas gangrene (Clostridial myonecrosis), Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome (HPS), *Helicobacter pylori* infection, Hemolytic-uremic syndrome (HUS), Hemorrhagic fever with renal syndrome (HFRS), Hepatitis A, Hepatitis B, Hepatitis C, Hepatitis D. Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr Virus Infectious Mononucleosis (Mono), Influenza (flu), Isosporiasis, Kawasaki disease, Keratitis. Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Melioidosis (Whitmore's disease), Meningitis, Meningococcal disease, Metagonimiasis, Microsporidiosis, Molluscum contagiosum (MC), Mumps, Murine typhus (Endemic typhus), *Mycoplasma* pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice)m Pediculosis pubis (Pubic lice, Crab lice), Pelvic inflammatory disease (PID), Pertussis (Whooping cough), Plague, Pneumococcal infection, *Pneumocystis* pneumonia (PCP), Pneumonia, Poliomyelitis, *Prevotella* infection, Primary amoebic meningoencephalitis (PAM), Prion disease, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), methicillin-resistant *staphylococcus aureus* infection (MRSA), Methicillin-sensitive *Staphylococcus aureus* infection (MSSA), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (*Pityriasis versicolor*), Toxocariasis, Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, viral infections, Viral pneumonia, West Nile Fever, White piedra (Tinea blanca), *Yersinia pseudotuberculosis* infection, yeast infections, Yersiniosis, Yellow fever, Zygomycosis.

In general, metabolic disorders or diseases refer to any disorder characterized by metabolic dysfunction. Metabolic disorders can be inherited. Non-limiting examples of inherited metabolic disorders include, e.g., Lysosomal storage disorders such as, e.g., lipid storage disorders, gangliosidosis, leukodystrophies, mucopolysaccharidoses, glycoprotein storage disorders, mucolipidoses, Hurler syndrome, Hunter Syndrome Niemann-Pick disease, Tay-Sachs disease, Gaucher disease, Fabry disease, Krabbe disease, Galactosemia, Maple syrup urine disease, Phenylketonuria (PKU), Glycogen storage diseases, Mitochondrial disorders, Friedreich ataxia, Peroxisomal disorders, such as, e.g., Zellweger syndrome, Adrenoleukodystrophy, Wilson disease, Hemochromatosis, Organic acidemias such as, e.g., methylmalonic acidemia and propionic acidemia, Urea cycle disorders such as, e.g., ornithine transcarbamylase deficiency and citrullinemia. Metabolic disorders can also be non-inherited, such as, e.g., hypercholesterolemia, hypertension, insulin resistance, type II diabetes, obesity syndrome, and metabolic syndrome.

In some embodiments, the disorder is an inflammatory disorder. Inflammatory disorders generally refer to any disorders associated with inflammatory response abnormalities. Inflammatory disorders are thought to underlie a vast variety of human diseases. Non-immune diseases with etiological origins in inflammatory processes include, e.g., cancer, cardiovascular disorders, neurological disorders, gastrointestinal disorders, metabolic disorders, among others. Non-limiting examples of inflammatory disorders include, e.g., Acne vulgaris, Asthma, Autoimmune disease, aortic valve stenosis, Celiac disease, Chronic prostatitis, Glomerulonephritis, Hypersensitivities, Inflammatory bowel diseases, lupus, multiple sclerosis, Pelvic inflammatory disease, Reperfusion injury, arthritis, Rheumatoid arthritis, fibromyalgia, Sarcoidosis, Transplant rejection, Vasculitis, and Interstitial cystitis, among others.

In some embodiments, the disorder is a disorder associated with overexpression or overactivation of HIF-1α or HIF-1α inducible genes. In some embodiments, the disorder is associated with HIF-1α overexpression or overactivation. Non-limiting examples of disorders associated with HIF-1α overexpression or overactivation include, e.g., pre-eclampsia, cancer, non-limiting examples of which are provided herein, Von Hippel-Lindau Kidney Disease, cardiomyopathy, inflammatory diseases such as inflammatory bowel disease, among others. In other embodiments, the disorder is a disorder associated with overexpression or overactivation of HIF-1α inducible genes, non-limiting examples of which are provided herein. Disorders that are associated with overexpression or overactivation of HIF-1α inducible genes include, e.g., cancer, non-limiting examples of which are provided herein, rheumatoid arthritis, diabetic retinopathy, wet form age-related macular degeneration.

Dosage Forms

A compound described herein can be delivered in the form of pharmaceutically acceptable compositions which comprise a therapeutically effective amount of one or more compounds described herein and/or one or more additional therapeutic agents such as a chemotherapeutic, formulated together with one or more pharmaceutically acceptable excipients. In some instances, the compound described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described above. Generally, doses of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg.

In some embodiments, a compound as disclosed herein is administered in a single dose. Typically, such administration will be by injection, e.g., intravenous injection, in order to introduce the agent quickly. However, other routes can be used as appropriate. A single dose of a compound as provided herein can also be used for treatment of an acute condition.

In some embodiments, a compound as provided herein is administered in multiple doses. Dosing can be about once, twice, three times, four times, five times, six times, or more than six times per day. Dosing can be about once a month, once every two weeks, once a week, or once every other day. In another embodiment a compound as disclosed herein and another agent are administered together about once per day to about 6 times per day. In another embodiment the administration of a compound as disclosed herein and an agent continues for less than about 7 days. In yet another embodiment the administration continues for more than about 6, 10, 14, 28 days, two months, six months, or one year. In some cases, continuous dosing is achieved and maintained as long as necessary.

In some embodiments, the compounds can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

Combination Therapy

The present disclosure also provide methods for combination therapies in which an agent known to modulate other pathways, or other components of the same pathway, or even overlapping sets of target enzymes are used in combination with a compound as disclosed herein, or a pharmaceutically acceptable salt, ester, prodrug or derivative thereof. In one aspect, such therapy includes but is not limited to the combination of the subject compound with chemotherapeutic agents, therapeutic antibodies, and radiation treatment, to provide a synergistic or additive therapeutic effect.

In some embodiments of the use of the compounds described herein for combination therapy, other agents are administered in the same pharmaceutical composition. In some embodiments of the use of the compounds described herein for combination therapy, other agents are not administered in the same pharmaceutical composition, but rather are administered simultaneously with the composition of the compound(s) described herein. In yet other embodiments, the other agents may be administered at different times. In some embodiments, because of differences in physical and chemical characteristics of the compound(s) described herein and the other agents, the compound(s) and other agents may be administered by different routes. The determination of the mode of administration and the advisability of administration in the same pharmaceutical composition is well within the knowledge of one skilled in the art, e.g., a physician. The initial co-administration can be made according to established protocols known in the art, and then, based upon the observed effects, the dosage, modes of administration and times of administration can be modified by the skilled clinician.

Additional agents may be, by way of non-limiting example only, small molecules, nutraceuticals, vitamins, e.g., vitamin D, drugs, pro-drugs, biologics, peptides, peptide mimetics, antibodies, antibody fragments, cell or tissue transplants, vaccines, polynucleotides such as DNA molecules, RNA molecules, (i.e.-siRNA, miRNA), antibodies conjugated to drugs, toxins, fusion proteins, chemotherapeutic agents. Agents may be delivered by vectors, including but not limited to: plasmid vectors, viral vectors, non-viral vectors, liposomal formulations, nanoparticle formulations, toxins, therapeutic radioisotopes, etc.

In some embodiments, the compounds or pharmaceutical composition as disclosed herein can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126, and Zosuquidar.

In some embodiments, the compounds or pharmaceutical compositions can be used in combination with commonly prescribed drugs for treatment of autoimmune diseases including but not limited to Enbrel®, Remicade®, Humira®, Avonex®, and Rebif®.

In some embodiments, the compounds or pharmaceutical compositions can be used in combination with commonly prescribed drugs for treatment of metabolic diseases including but not limited to Carglumic acid (Carbaglu®), Arginine, Citrulline, Carglumic acid, Sodium benzoate, Sodium phenylbutyrate, L-tryptophan, Dextromethorphan, Ketamine, Thiamine, Carnitine, and Glycine.

In some embodiments, the compounds or pharmaceutical compositions can be used in combination with commonly prescribed drugs for treatment of infectious diseases. Non-limiting examples of drugs for the treatment of infectious diseases include, e.g., antibiotics, anti-fungals, anti-yeast agents, antivirals, atovaquone-proguanil-oral (Malarone), cefadroxil (Duricef), cefprozil (Cefzil), ciprofloxacin (Cipro, Cipro XR, Proquin XR), fluconazole (Diflucan), levofloxacin (Levaquin), loracarbef (Lorabid), nitrofurantoin (Furadantin, Macrobid, Macrodantin), tetracycline (Sumycin)

In some embodiments, the compounds or pharmaceutical compositions can be used in combination with commonly prescribed drugs for treatment of inflammatory disorders, non-limiting examples of which include histamine, histamine antagonists, bradykinin, bradykinin antagonists, eicosanoids, prostaglandins, thromboxanes, leukotrienes, aspirin, anti-inflammatory agents, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, agents that target cytokines which mediate interactions involved in humoral and cellular immune responses, lipid-derived autacoids, β-adrenergic agonists, ipratropium, glucocorticoids, methylxanthines, acetaminophen, ibuprofen, aspirin, leukotriene inhibitors, steroids, glucocorticoids, any combinations thereof, or others. The present invention may be further illustrated by reference to the following examples.

EXAMPLES

Example 1—Synthesis of Morpholine-Based Oxopiperazines

The synthesis of morpholine-based oxopiperazine 1.7 may commerce with amine 1.1, which is coupled to hydroxyacid 1.2 to give coupling product 1.3. Cyclization of compound 1.3 can be achieved under suitable conditions, for example, by using 1,2-dibromoethane and a base, such as NaH, to give morpholine acid 1.4 upon hydrolysis. Morpholine acid 1.4 can then be coupled with piperazine 1.5 to give ester 1.6, which can be readily converted to primary amide 1.7.

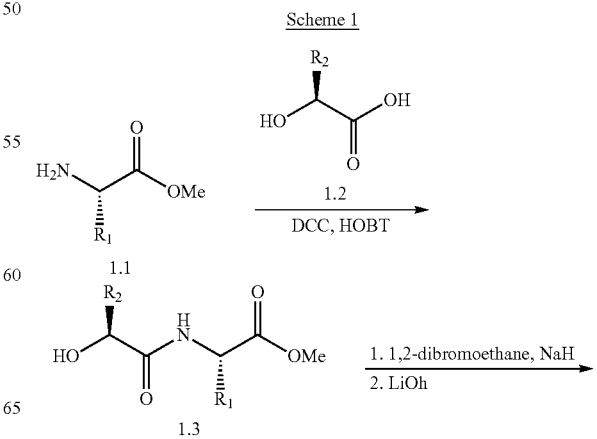

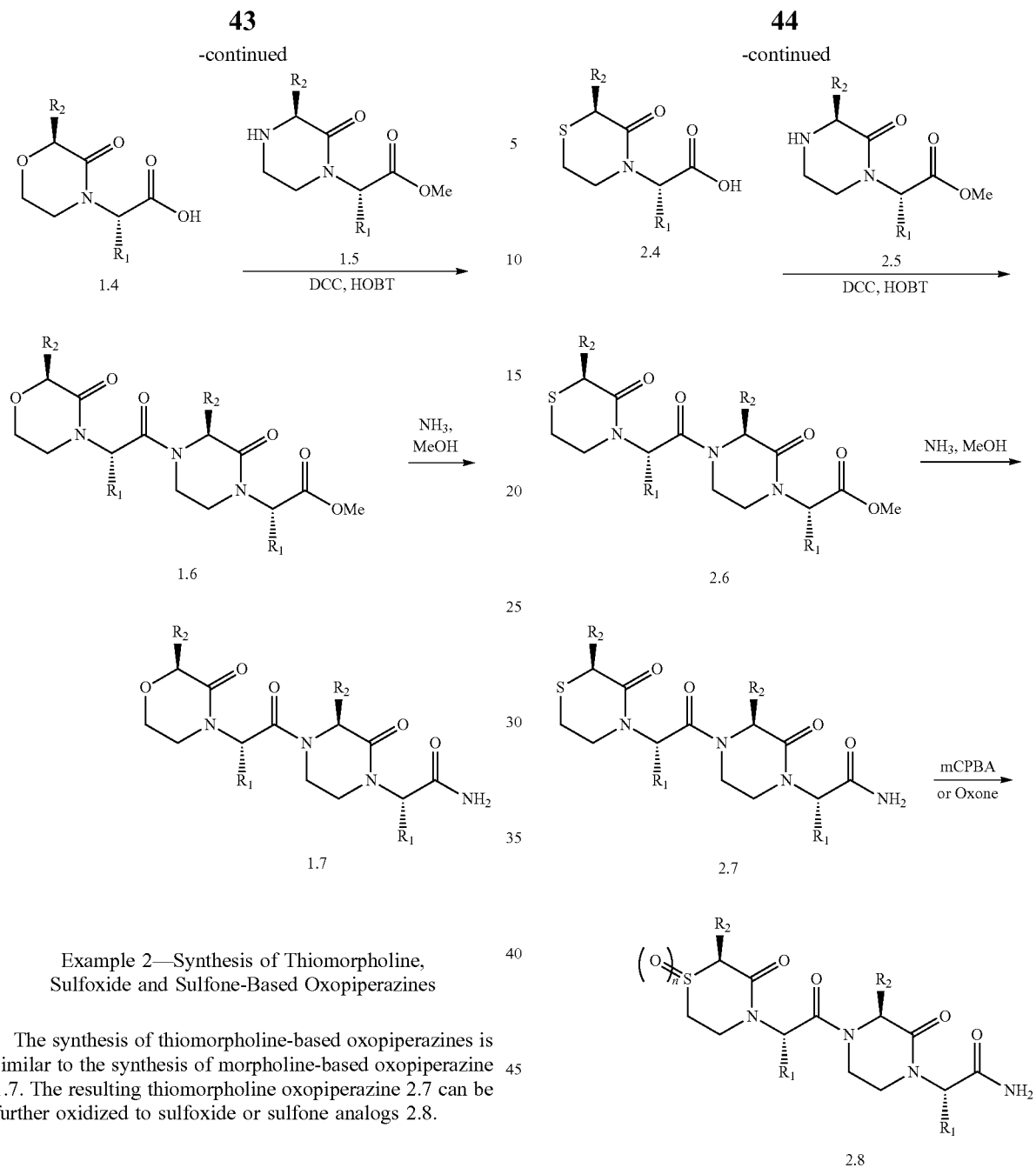

Example 2—Synthesis of Thiomorpholine, Sulfoxide and Sulfone-Based Oxopiperazines The synthesis of thiomorpholine-based oxopiperazines is similar to the synthesis of morpholine-based oxopiperazine 1.7. The resulting thiomorpholine oxopiperazine 2.7 can be further oxidized to sulfoxide or sulfone analogs 2.8.

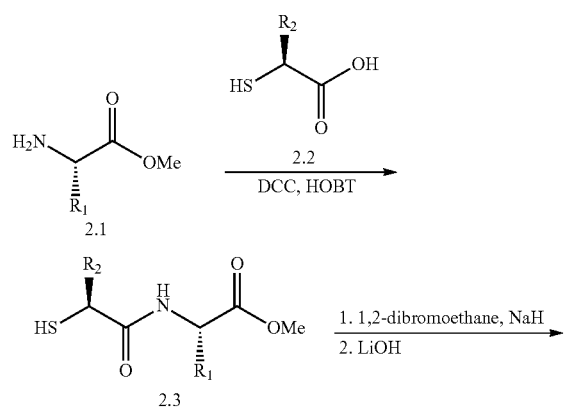

n = 1 or 2

Example 3—Synthesis of Oxopiperazine Analogs with Natural or Unnatural Amino Acids Scheme 3 outlines a synthetic route leading to oxopiperazines from natural and unnatural amino acids. Monoallylation of amino acid methyl ester 3.1 followed by coupling with acid 3.3 will give dipeptide 3.4. Cleavage of the ally group followed by reductive cyclization can install the requisite piperazine ring to give compound 3.5, which can be transformed to target 3.9.

Scheme 3

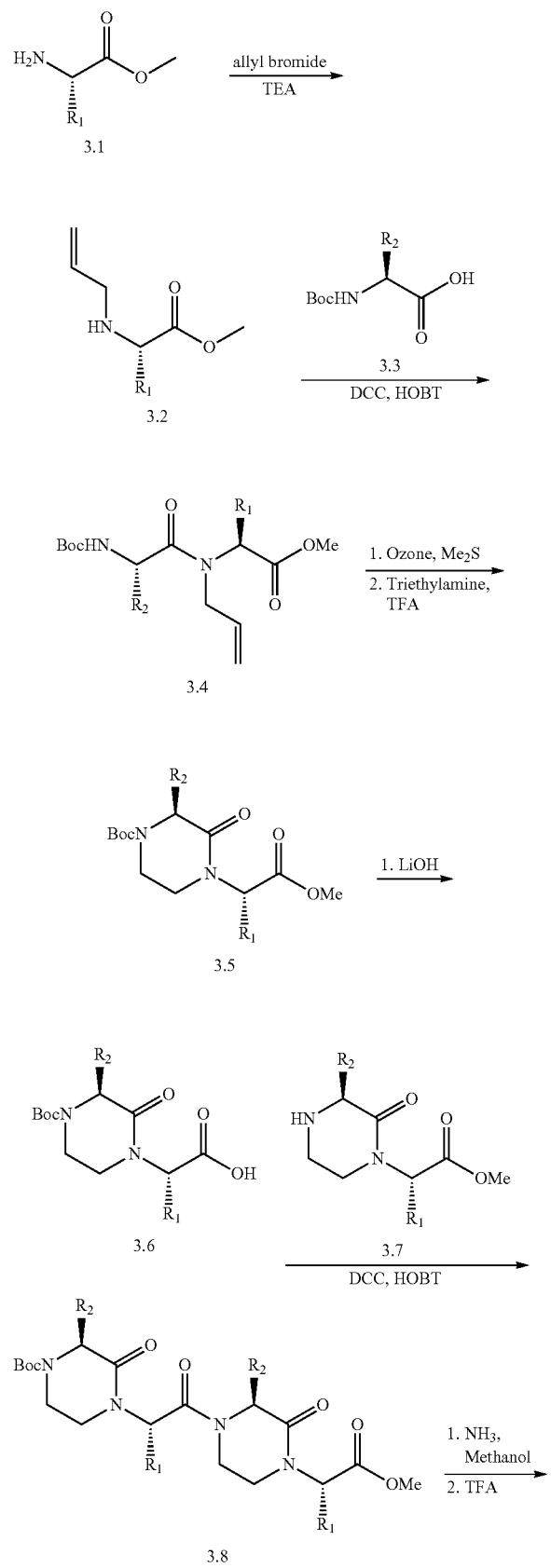

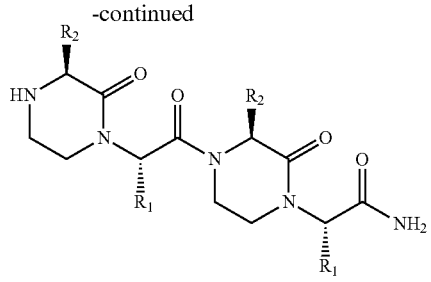

Example 4—Synthesis of Oxopiperazine Analogs with Extended Enedione Moiety

The synthesis may commence with protected amino ketone 4.1. Condensation of ketone 4.1 with ketone R₂COCN will provide dione 4.2. Activation of dione 4.2 followed by transition-metal catalyzed carbonylation gives ene-one acid 4.3, which may be converted to piperazine 4.5 via coupling and deprotection of Boc. Similarly, the morpholine and thiomorpholine analogs of compound 4.5 can be synthesized.

Scheme 4

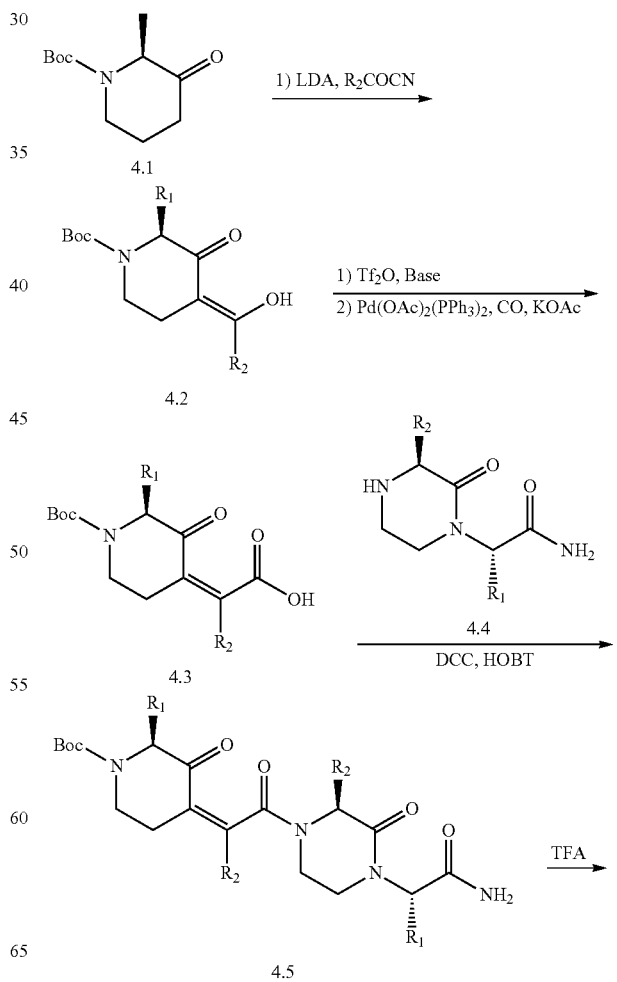

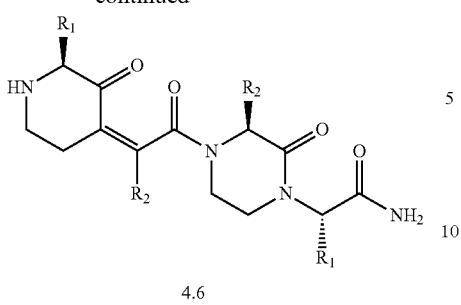

4.6

Example 5—Synthesis of Oxopiperazine Analogs with Alkene Linker

The synthesis may commence with ketone 5.1. Installation of an alkene linker may be accomplished with an olefination reaction, for example, a Wittig Olefination reaction, to give olefin 5.4. Allylic bromination of compound 5.4 followed by coupling with compound 5.6 may yield the desired product 5.7. The morpholine and thiomorpholine analogs of compound 5.6 can be similarly synthesized.

Scheme 5

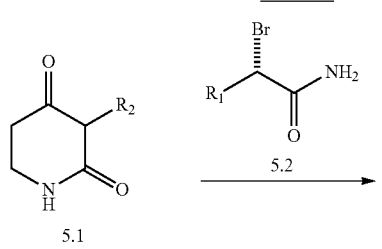

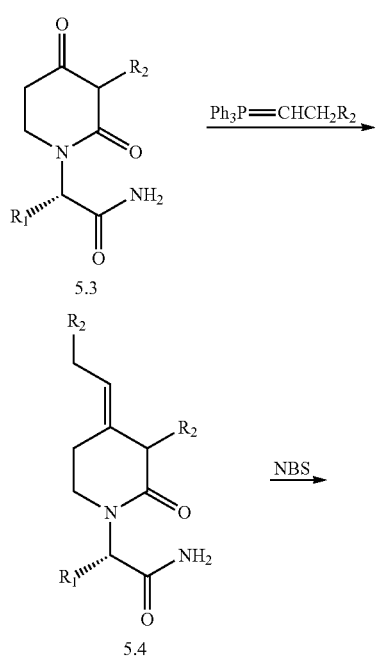

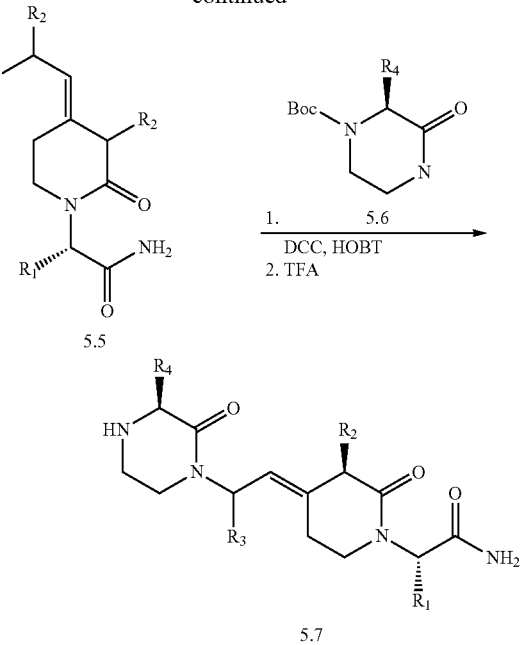

Example 6—Synthesis of Oxopiperazine Analogs with Fused Heterocyclic Rings

The synthesis of compound 5.1 with a fused heterocyclic rings may be accomplished via a sequence of hydrogenation and cyclization with, for example, Lawesson's reagent. This chemistry allows the synthesis of analogs with X=N, S or O.

Scheme 6

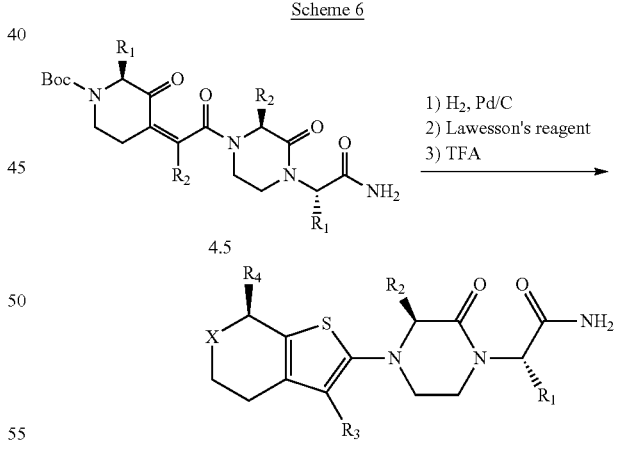

Example 7—Synthesis of Ring-Expanded Oxopiperizine Analogs

As outlined in scheme 7, ring expanded oxopiperazine analogs may be synthesized using similar chemistry as the synthesis of compound 3.9, except by substituting allyl bromide with homoallyl bromide for the synthesis of 7-membered ring analog 7.1 and bishomoallyl bromide for the synthesis of 8-membered ring analogs. Similarly, the morpholine and thiomorpholine analogs may be synthesized.

Example 8—Synthesis of Oxopiperazine Analogs with a Substituted Heteroaromatic Ring Outlined in Scheme 8 is a proposed synthesis of oxopiperazine analogs with a substituted heteroaromatic ring. The stereogenic center attached to the $R_1$ group can be installed with Evans' chrial oxazolidinone chemistry (see, D. A. Evans et al. *Journal of the American Chemical Society*, 1981, 213, 2127) to give the chiral building block 8.4, which can be further converted to target 8.6. The heteroaryl with an additional substituent on the ring can be synthesized using ortholithiation chemistry. For example, a hydroxyl group can be installed by trapping the lithio species with pinacole boronate followed by oxidation to give acid 8.7, which can be converted to the target 8.10.

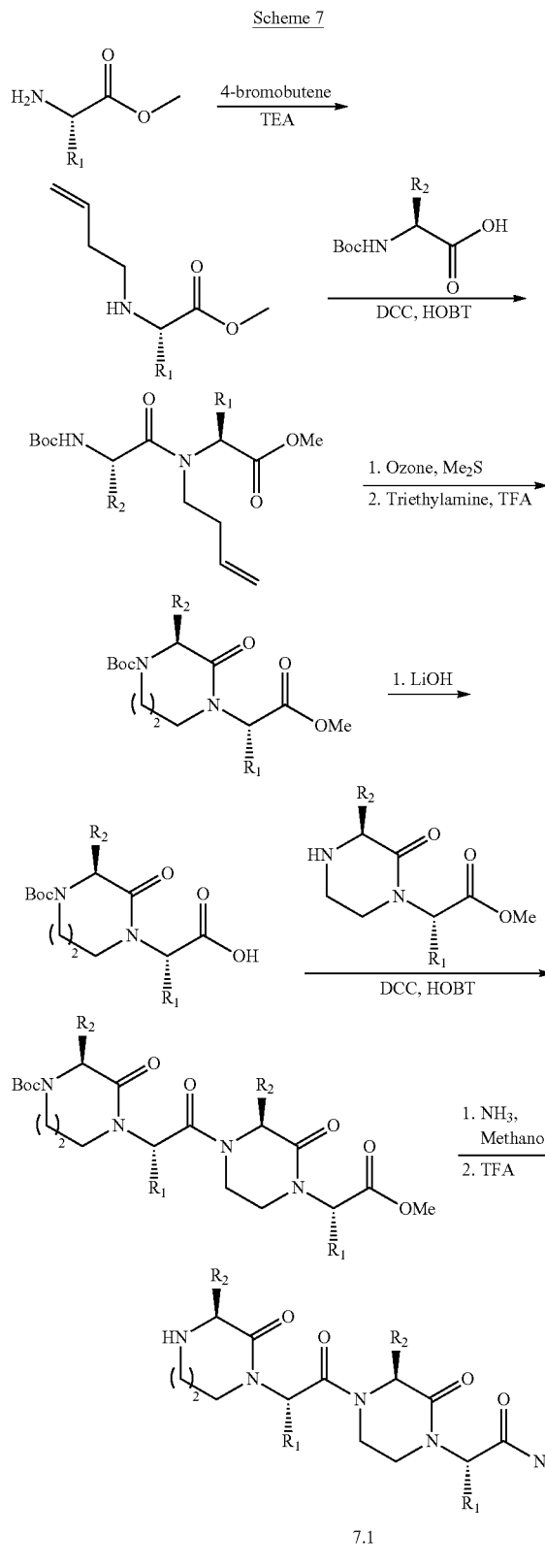

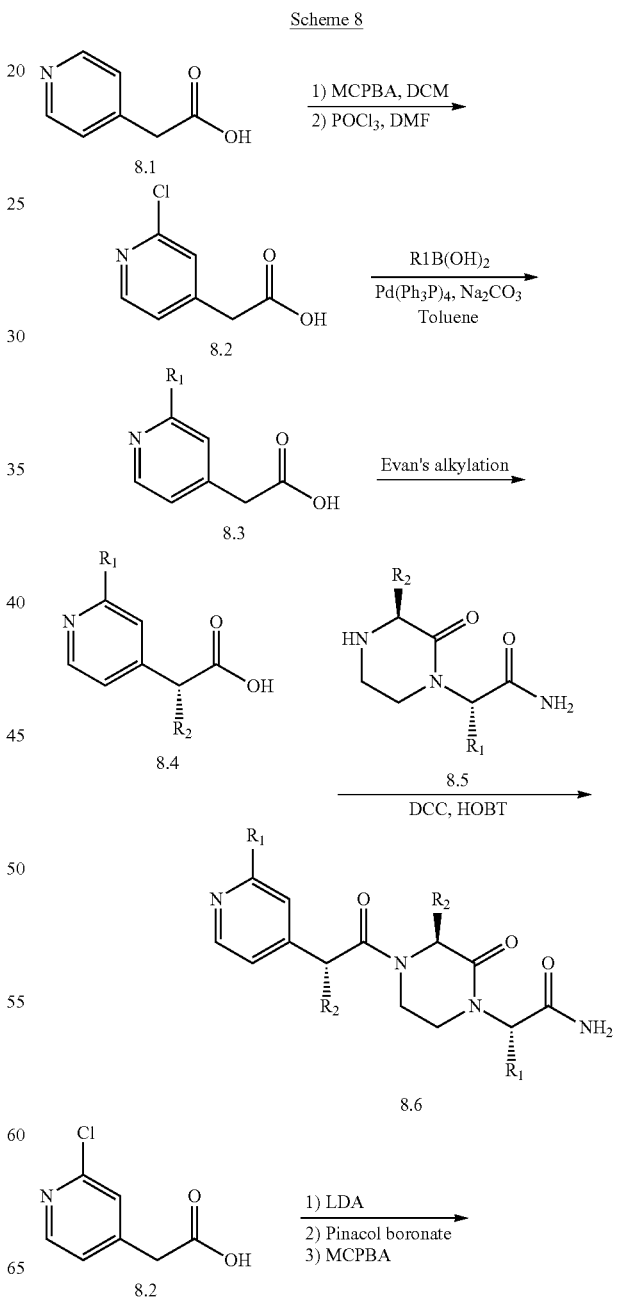

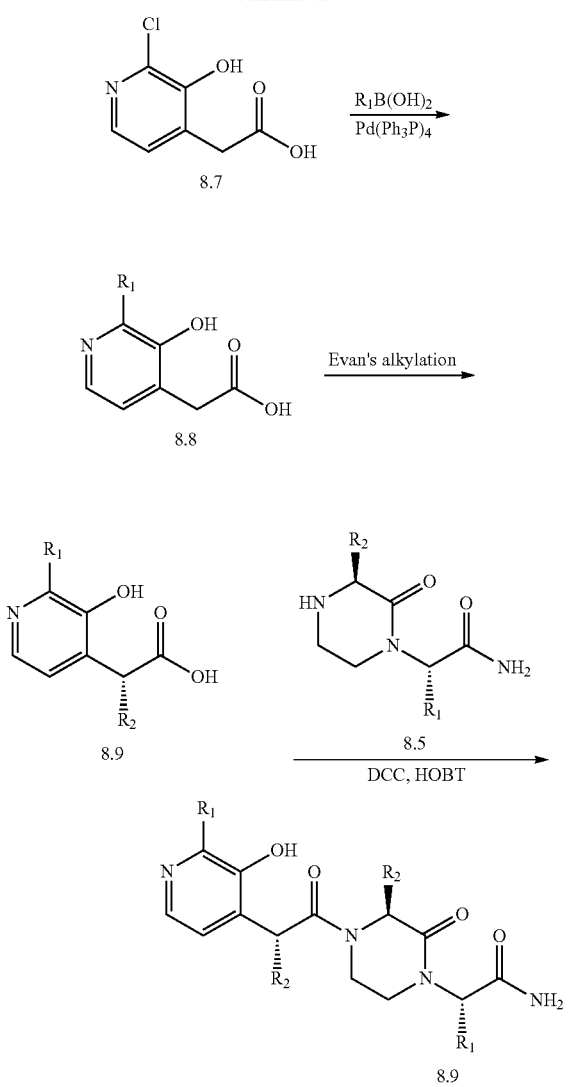

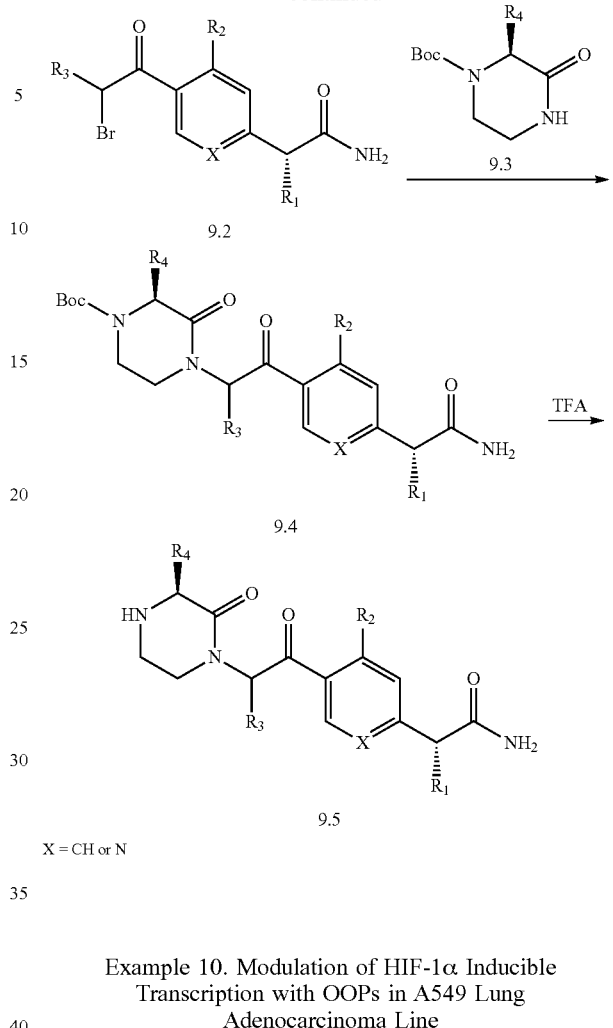

X = CH or N

Example 9—Synthesis of Oxopiperazine Analogs with a Substituted Aromatic or Heteroaromatic Ring The synthesis of target 9.5 may commence with substituted aryl or heteroaryl 9.1. α-Bromination of the ketone moiety followed by coupling with oxopiperazine 9.3 yields the desired product 9.5 after Boc deprotection.

Scheme 9

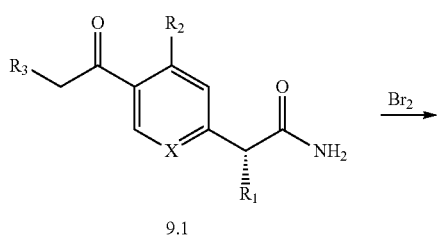

Example 10. Modulation of HIF-1α Inducible Transcription with OOPs in A549 Lung Adenocarcinoma Line A549 cells, a non-small cell lung adenocarcinoma cell line, were used. It has been reported that A549 cell line produces robust upregulation of key HIF-inducible genes under hypoxia conditions. Specifically, Comoglio et all reported that under hypoxia c-Met mRNA level is significantly upregulated in A549 cell line. A549 cells were maintained in 2% serum followed by treating cells with compound or control in the media with 0.2% serum for 48 h.

LOX (lysyl oxidase) is another gene that is up-regulated under hypoxia and the protein is involved in regulating the extracellular matrix during invasive behavior and metastasis of cancer tissue. LOX gene showed better induction with hypoxia bag after 48 h and showed significant down-regulation in the transcriptional activity after treatment with OOPS.

Figure 1:
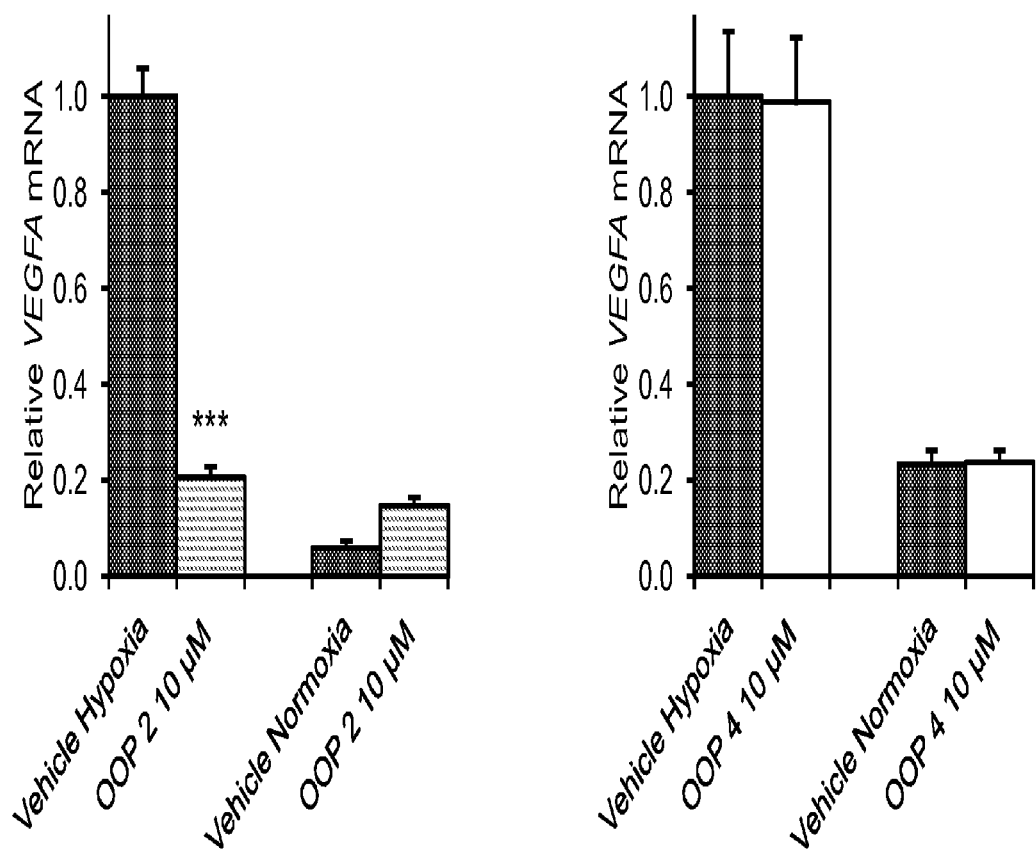
FIG. 1 shows that OOPS down-regulates hypoxia-induced transcription in cell culture. OOP 2 reduced expression levels of VEGFA gene in A549 cells under hypoxia conditions as measured by real-time qRT-PCR. Hypoxia was mimicked by $O_2$ deprivation in a GasPak™ EZ Anaerobe Pouch System (BD). OOP 4 is a negative control with no inhibitory activity at the same concentrations. Error bars are ±s.e.m. of four independent experiments. *** P<0.001, t-test.
Figure 2:
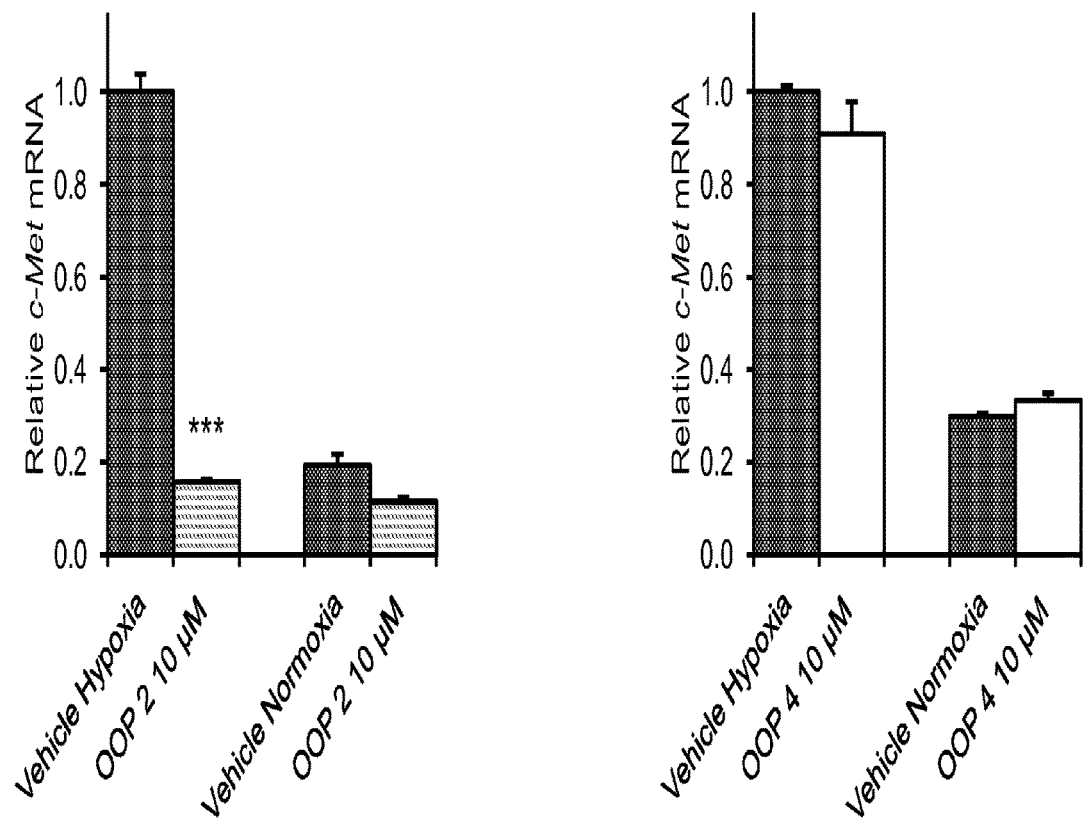
FIG. 2 shows that OOP down-regulates hypoxia-induced transcription in cell culture. OOP 2 reduced expression levels of c-Met gene in A549 cells under hypoxia conditions as measured by real-time qRT-PCR. Hypoxia was mimicked by $O_2$ deprivation in a GasPak™ EZ Anaerobe Pouch System (BD). OOP 4 is a negative control with no inhibitory activity at the same concentrations. Error bars are ±s.e.m. of four independent experiments. *** P<0.001, t-test.
Figure 3:
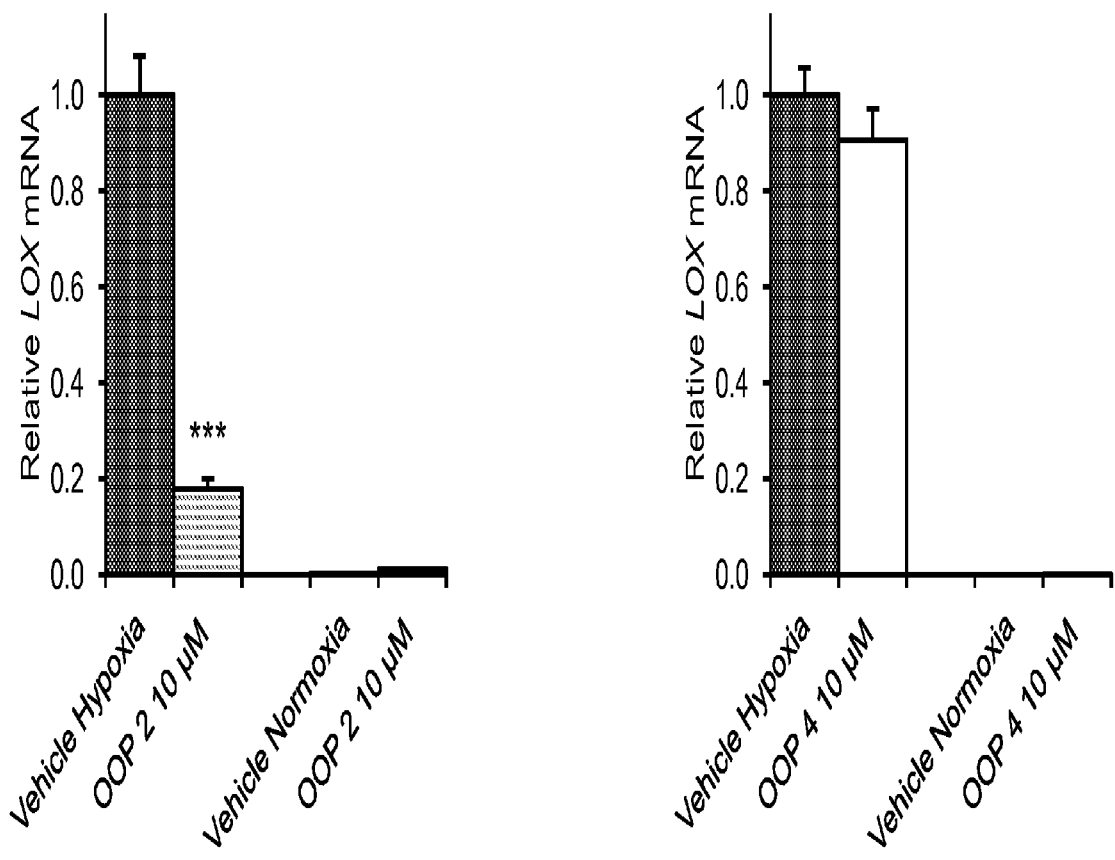
FIG. 3 shows that OOP down-regulates hypoxia-induced transcription in cell culture. OOP 2 reduced expression levels of LOX gene in A549 cells under hypoxia conditions as measured by real-time qRT-PCR. Hypoxia was mimicked by $O_2$ deprivation in a GasPak™ EZ Anaerobe Pouch System (BD). OOP 4 is a negative control with no inhibitory activity at the same concentrations. Error bars are ±s.e.m. of four independent experiments. *** P<0.001, t-test.
Figure 4:
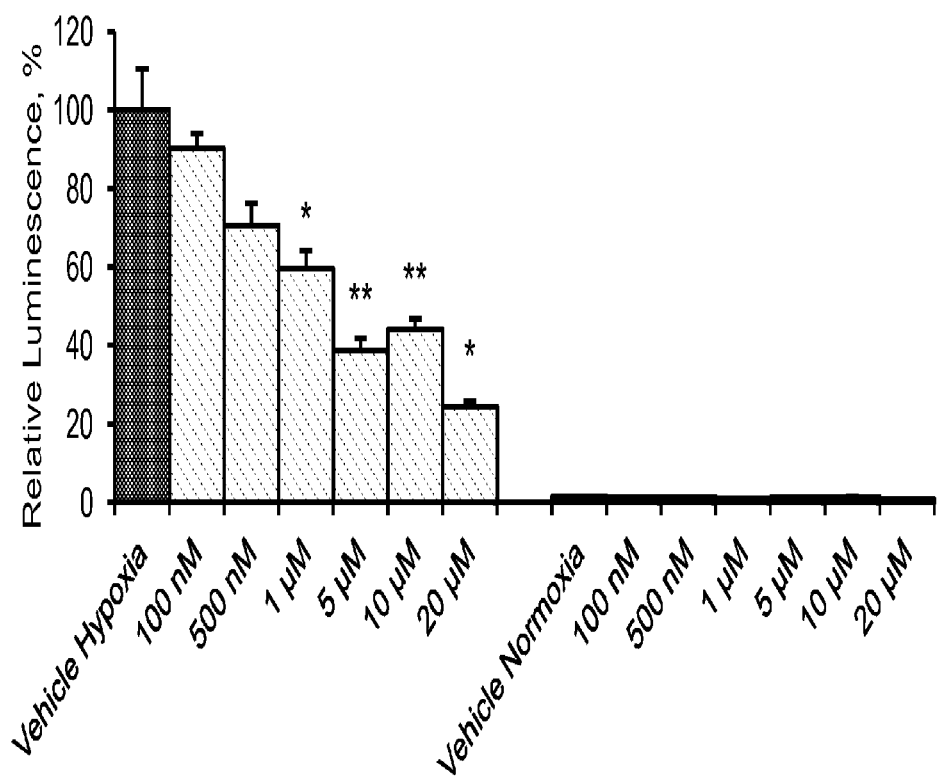
FIG. 4 shows that OOP 1 reduces HIF1α-inducible promoter activity in vitro in a dose-dependent manner. Results from the luciferase-based promoter activity assay with MDA-MB-231-HRE-Luc cell line treated with OOP 1 at various concentration. Hypoxia was mimicked by $O_2$ deprivation in a GasPak™ EZ Anaerobe Pouch System (BD).

Quantitative Real-Time PCR:

mRNA levels of three HIF-1α inducible genes: VEGF, c-Met and Glut1 in A549 cells after treatment with OOPS were measured. Data from qRT-PCR experiments showing mRNA levels of three HIF-1α inducible genes, VEGF, c-Met and LOX in A549 after treatment of the cells in a medium with OOPS is described in FIGS. 1-3. Hypoxia was mimicked by O2 deprivation in a GasPak™ EZ Anaerobe Pouch System (BD). Error bars are ±s.e.m for the experiments performed in quadruplicate. Error bars are ±s.e.m. of experiments performed in triplicate. * P<0.001,  P<0.01, t test.

Example 11. OOPs Reduces HIF1α-Inducible Promoter Activity In Vitro in a Dose-Dependent Manner An analysis of hypoxia-inducible promoter activity was performed using luciferase assays in a MDA-MB-231 cell line stably transfected with hRE-hCMV-Luc plasmid. Cell lines were treated with OOP compounds at various concentrations. Hypoxia was mimicked by $O_2$ deprivation in a GasPak™ EZ Anaerobe Pouch System (BD). Error bars represent ±s.e.m. of experiments performed in triplicates. Results are shown in FIGS. 4-7.

Example 12. Intracellular Levels of HIF-1α and c-Met Following Treatment Using OOPs The effect of OOPS on HIF-1α and c-met protein levels was studied. A549 cells were treated with OOPS. Cells were incubated for a total of 24 hours with OOP 2. After 6 h, hypoxia was mimicked by O2 deprivation in a GasPak™ EZ Anaerobe Pouch System (BD) for an additional 18 hours. Western blots were done and bar graphs for the protein levels are shown in FIGS. 8 and 9.

Example 13. Cytotoxicity Assays

One potential issue that arises with the use of transcriptional inhibitors is their cytotoxicity. Therefore, careful assessment of the cytotoxicity is important to evaluate nonspecific, global effects on transcriptional machinery. Cytotoxicity experiments were performed in order to obtain the EC50 values of OOPS in an MCF7 breast cancer cell line. The goal was to determine the window of viable concentrations and perform our transcription inhibition experiments at concentrations significantly below the EC50 values in these cell lines.

The cells were treated with different concentrations of compound for 48 hours in serum free F-12K medium. The cells are plated into 96-well dishes (Greiner) at a density of 5,000-10,000 cells/well in 200 μl of the cell culture media prepared as recommended by the vendor (ATCC). The plates are then placed into the incubator (37° C., 5% $CO_2$) until the desired confluence is reached (in ca. 24-72 hours). Next, the media in all wells is replaced with the solution of the OOPS compound (150 μl for 48 hour study, 200 μl for 72 hour study) in the appropriate cell culture medium. The plates are then incubated for 48 hours (37° C., 5% $CO_2$). After 48 hours of incubation with the compound, MTT (5 mg/ml in PBS, Sigma-Aldrich) is added into every well (10% v/v) and mixed thoroughly and carefully. The plates are further incubated for 3-4 hours (37° C., 5% $CO_2$), then the media is removed. The resulting purple precipitate is then dissolved in DMSO (200 μl/well) and the absorption of the metabolite product (purple formazan) in each well is measured at 562 nm using microplate reader (BioTek Synergy II). The absorption values are plotted against the concentration of the compound and $GI_{50}$ is determined. Results are shown in FIGS. 10 and 11.

Example 14. Gene Expression Profiling and Microarray Analysis

Target proteins p300 and CBP are pleiotropic multidomain coactivators, and their CH1 regions contain binding sites for multiple transcription factors. To determine non-specific genome-wide effects of OOPS, in vitro gene expression profiling experiments were conducted with OOPS using Affymetrix Human Gene ST 1.0 Arrays containing oligonucleotide sequences representing 28,869 transcripts. In order to interrogate cellular genome for global effects, MCF7 cells were treated with OOPS. Results are shown in FIG. 12.

Example 15. Maximum Tolerated Dose (MTD) Study

Balb/C mice were used in an MTD experiment. 1 mouse was present in the vehicle group and 3 mice in OOP 2-treated group. Food and water ad libitum was provided as needed and according to the protocol. OOP 2 was administered by Intraperitoneal (IP) injection. OOP 2 was dissolved in sterile PBS at a concentration range between 2-100 mg. Volume administered was about 100-150 μl every 48 hours. No toxicity was seen even at 100 mg/kg of OOP 2, at which point the experiment was terminated. Results are shows in FIG. 13 ("LLAQ"=OOP 2).

Example 16. Mouse Xenograft Study

The mouse model used was the nude mouse available from Taconic, Inc. Safety and efficacy of OOPS in 786-0 cells growing as tumors in mouse xenograft models was evaluated. The primary endpoint of efficacy (reduction in tumor volume of >50% as compared to control) and the secondary endpoint of survival (Kaplan-Meier) when treated with OOP 2 in PBS the above mentioned cell line at 20 mg/kg given intro tumorally every other day was evaluated. Tumors were established in the flank region and grown to 60-100 mm³.

Animals were weighed daily during drug administration for signs of toxicity and weekly thereafter, and tumor volume measured with calipers twice weekly. Animals that appear moribund or when tumor mass approaches 20% body weight will be euthanized, otherwise studies will be continued for 45 days. Euthanasia was performed in a chamber containing CO2 as recommended by the American Veterinary Panel on Euthanasia (AVMA 202229-249, 1993). The mice were housed in an A.L.A.C.C. approved barrier facility under the direct supervision of a professional veterinarian. Results are shown in FIG. 14.

While various embodiments of the present invention have been shown and described herein, it will be obvious to those skilled in the art that such embodiments are provided by way of example only. Numerous variations, changes, and substitutions will now occur to those skilled in the art without departing from the invention. It is intended that the following claims define the scope of the invention and that methods and structures within the scope of these claims and their equivalents be covered thereby.

What is claimed is:

1. A method of treating cancer in a subject comprising administering to the subject a therapeutically effective amount of a compound of Formula I, or a pharmaceutically acceptable salt thereof, having the structure:

Formula I

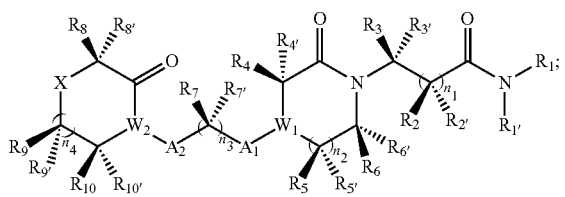

wherein
each $R_1$ and $R_{1'}$ is independently selected from the group consisting of H, alkyl, cycloalkyl and heteroalkyl, or $R_1$ and $R_{1'}$ and the N to which they are attached form the structure

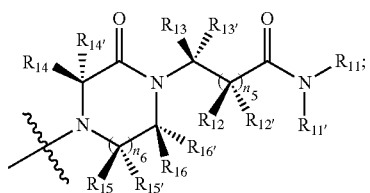

each $R_{11}$ and $R_{11'}$ is independently selected from the group consisting of H, alkyl, cycloalkyl and heteroalkyl;
each $n_1$, $n_3$ and $n_5$ is independently 0 or 1;
each $n_2$ and $n_6$ is independently 0, 1, 2 or 3;
$n_4$ is 1;
$A_1$-$W_1$ is

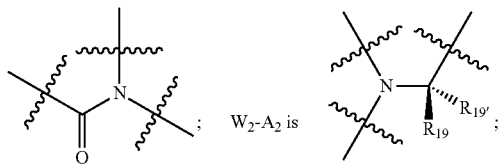

each $R_2$, $R_{2'}$, $R_3$, $R_{3'}$, $R_4$, $R_{4'}$, $R_5$, $R_{5'}$, $R_6$, $R_{6'}$, $R_7$, $R_{7'}$, $R_8$, $R_{8'}$, $R_9$, $R_{9'}$, $R_{10}$, $R_{10'}$, $R_{12}$, $R_{12'}$, $R_{13}$, $R_{13'}$, $R_{14}$, $R_{14'}$, $R_{15}$, $R_{15'}$, $R_{16}$, $R_{16'}$, $R_{19}$ and $R_{19'}$ is independently selected from the group consisting of H, alkyl, cycloalkyl, heteroalkyl, alkylamine, alkylhydroxyl, alkylthiol, alkylcarboxylic acid, alkylamide, alkylguanidine, aryl, heteroaryl, alkylaryl, alkylheteroaryl and an amino acid side chain, wherein the amino acid is alanine, arginine, aspartic acid, cysteine, glutamine, glutamic acid, glycine, histidine, isoleucine, leucine, lysine, methionine, phenylalanine, proline, serine, threonine, tryptophan, tyrosine, or valine;
X is selected from the group consisting of —$NR_{21}$, —$NC(=O)R_{22}$, —$NS(=O)_2NR_{23}R_{24}$, —$NS(=O)_2R_{25}$ and —$NC(=O)NR_{26}R_{27}$;
each $R_{21}$, $R_{22}$, $R_{23}$, $R_{24}$, $R_{25}$, $R_{26}$ and $R_{27}$ is independently selected from the group consisting of H, alkyl, cycloalkyl, heteroalkyl, aryl, heteroaryl, and any pair of $R_{23}/R_{24}$ and $R_{26}/R_{27}$ may optionally form a 5-8 membered, substituted or unsubstituted, saturated or unsaturated, heterocyclic ring; and when (i) each of $n_2$ and $n_6$ is 1; and (ii) each of $n_1$ and $n_3$ is 0; then X is selected from the group consisting of —$NS(=O)_2NR_{23}R_{24}$ and —$NS(=O)_2R_{25}$; wherein the cancer is acute leukemia, acute t-cell leukemia, acute lymphocytic leukemia, acute myelocytic leukemia, myeloblastic leukemia, promyelocytic leukemia, myelomonocytic leukemia, monocytic leukemia, erythroleukemia, chronic leukemia, chronic myelocytic (granulocytic) leukemia, chronic lymphocytic leukemia, polycythemia vera, Hodgkin's lymphoma, follicular lymphoma, non-Hodgkin's lymphoma, multiple myeloma, Waldenstrom's macroglobulinemia, fibrosarcoma, myxosarcoma, liposarcoma, chondrosarcoma, osteogenic sarcoma, lymphangiosarcoma, mesothelioma, Ewing's tumor, leiomyosarcoma, rhabdomyo sarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, lung carcinoma, small cell lung carcinoma, bladder carcinoma, epithelial carcinoma, glioma, craniopharyngioma, ependymoma, pinealoma, hemangioblastoma, acoustic neuroma, oligodendroglioma, meningioma, melanoma, neuroblastoma, retinoblastoma, endometrial cancer, non-small cell lung cancer, thymus cancer, brain cancer, skin cancer, intraocular melanoma, oral cavity cancer, oropharyngeal cancer, stomach cancer, kidney cancer, liver cancer, esophageal cancer, thyroid cancer, AIDS-related cancer, or viral-induced cancer.

2. The method of claim 1, wherein each of $R_1$ and $R_{1'}$ is H and $n_1$ is 0.

3. The method of claim 1, wherein each $n_2$ and $n_6$ is 1; each $n_1$, $n_3$, and $n_5$ is 0; and each $R_5$, $R_{5'}$, $R_6$, $R_{6'}$, $R_9$, $R_{9'}$, $R_{10}$, $R_{10'}$, $R_{15}$, $R_{15'}$, $R_{16}$, and $R_{16'}$ is H.

4. The method of claim 1, wherein the compound or pharmaceutically acceptable salt is a compound or a pharmaceutically acceptable salt of Formula Ia:

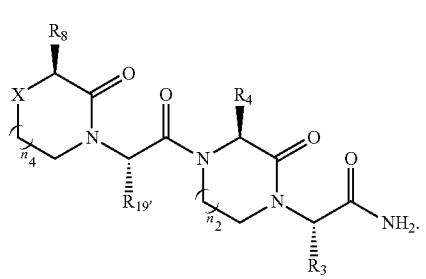

Formula Ia

5. The method of claim 1, wherein the compound or pharmaceutically acceptable salt is a compound or a pharmaceutically acceptable salt of Formula Id:

Formula Id

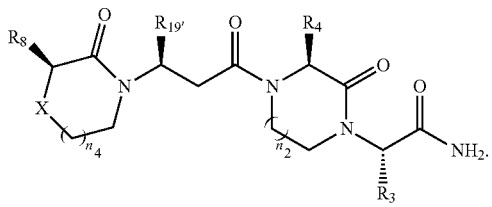

6. The method of claim 4 or 5, wherein X is NH.
7. The method of claim 4 or 5, wherein $n_2$ is 1.
8. A method of inhibiting a protein-protein interaction, comprising contacting at least one of the proteins involved in said protein-protein interaction with an effective amount of a compound of Formula I, or a pharmaceutically acceptable salt, having the structure:

Formula I

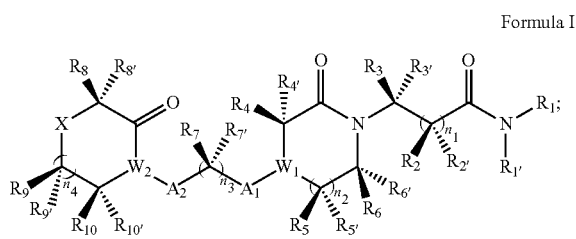

wherein
each $R_1$ and $R_{1'}$ is independently selected from the group consisting of H, alkyl, cycloalkyl and heteroalkyl, or
$R_1$ and $R_{1'}$ and the N to which they are attached form the structure

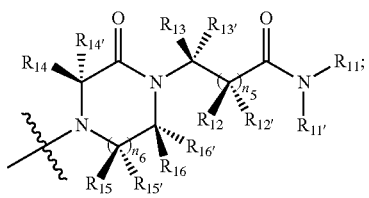

each $R_{11}$ and $R_{11'}$ is independently selected from the group consisting of H, alkyl, cycloalkyl and heteroalkyl;
each $n_1$, $n_3$ and $n_5$ is independently 0 or 1;
each $n_2$ and $n_6$ is independently 0, 1, 2 or 3;
$n_4$ is 1;
$A_1$-$W_1$ is

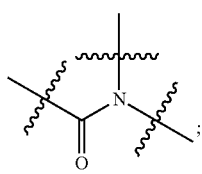 [SMILES: *C(=O)N(*)*]

$W_2$-$A_2$ is

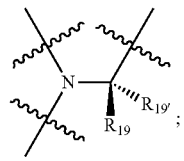

each $R_2$, $R_{2'}$, $R_3$, $R_{3'}$, $R_4$, $R_{4'}$, $R_5$, $R_{5'}$, $R_6$, $R_{6'}$, $R_7$, $R_{7'}$, $R_8$, $R_{8'}$, $R_9$, $R_{9'}$, $R_{10}$, $R_{10'}$, $R_{12}$, $R_{12'}$, $R_{13}$, $R_{13'}$, $R_{14}$, $R_{14'}$, $R_{15}$, $R_{15'}$, $R_{16}$, $R_{16'}$, $R_{19}$ and $R_{19'}$ is independently selected from the group consisting of H, alkyl, cycloalkyl, heteroalkyl, alkylamine, alkylhydroxyl, alkylthiol, alkylcarboxylic acid, alkylamide, alkylguanidine, aryl, heteroaryl, alkylaryl, alkylheteroaryl and an amino acid side chain, wherein the amino acid is alanine, arginine, aspartic acid, cysteine, glutamine, glutamic acid, glycine, histidine, isoleucine, leucine, lysine, methionine, phenylalanine, proline, serine, threonine, tryptophan, tyrosine, or valine;
X is selected from the group consisting of —$NR_{21}$, —NC(=O)$R_{22}$, —NS(=O)$_2$$NR_{23}$$R_{24}$, —NS(=O)$_2$$R_{25}$ and —NC(=O)$NR_{26}$$R_{27}$;
each $R_{21}$, $R_{22}$, $R_{23}$, $R_{24}$, $R_{25}$, $R_{26}$ and $R_{27}$ is independently selected from the group consisting of H, alkyl, cycloalkyl, heteroalkyl, aryl, heteroaryl, and any pair of $R_{23}/R_{24}$ and $R_{26}/R_{27}$ may optionally form a 5-8 membered, substituted or unsubstituted, saturated or unsaturated, heterocyclic ring; and
when (i) each of $n_2$ and $n_6$ is 1; and (ii) each of $n_1$ and $n_3$ is 0; then X is selected from the group consisting of —NS(=O)$_2$$NR_{23}$$R_{24}$ and —NS(=O)$_2$$R_{25}$; wherein at least one of the proteins involved in said protein-protein interaction is HIF-1α or HIF-2α.
9. The method of claim 8, wherein said at least one of the proteins comprises HIF-1α.
10. The method of claim 9, wherein said protein-protein interaction is HIF-1α-p300 interaction.
11. The method of claim 9, wherein said protein-protein interaction is HIF-1α-CREB-binding protein interaction.
12. The method of claim 1, wherein said cancer is multiple myeloma, Waldenstrom's macroglobulinemia, fibrosarcoma, myxosarcoma, liposarcoma, chondrosarcoma, osteogenic sarcoma, lymphangiosarcoma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, lung carcinoma, small cell lung carcinoma, bladder carcinoma, epithelial carcinoma, glioma, craniopharyngioma, ependymoma, pinealoma, hemangioblastoma, acoustic neuroma, oligodendroglioma, meningioma, melanoma, neuroblastoma, retinoblastoma, endometrial cancer, non-small cell lung cancer, thymus cancer, brain cancer, skin cancer, intraocular melanoma, oral cavity cancer, oropharyngeal cancer, stomach cancer, kidney cancer, liver cancer, esophageal cancer, thyroid cancer, AIDS-related cancer, or viral-induced cancer.

* * * * *